US011892411B2

(12) United States Patent
Liu et al.

(10) Patent No.: US 11,892,411 B2
(45) Date of Patent: Feb. 6, 2024

(54) QUANTITATIVE HORMONE AND CHEMICAL ANALYTE TEST RESULT SYSTEMS AND METHODS

(71) Applicant: Easy Healthcare Corporation, Burr Ridge, IL (US)

(72) Inventors: Xiaolian Liu, Burr Ridge, IL (US); Li Zou, Willowbrook, IL (US)

(73) Assignee: Easy Healthcare Corporation, Burr Ridge, IL (US)

( * ) Notice: Subject to any disclaimer, the term of this patent is extended or adjusted under 35 U.S.C. 154(b) by 0 days.

(21) Appl. No.: 17/976,403

(22) Filed: Oct. 28, 2022

(65) Prior Publication Data

US 2023/0048718 A1    Feb. 16, 2023

Related U.S. Application Data

(63) Continuation of application No. 17/337,068, filed on Jun. 2, 2021, now Pat. No. 11,519,909.
(Continued)

(51) Int. Cl.
| | |
|---|---|
| *G01N 21/78* | (2006.01) |
| *G01N 33/543* | (2006.01) |
| *G06T 11/20* | (2006.01) |
| *G01N 33/74* | (2006.01) |
| *G01N 33/76* | (2006.01) |
| *G06V 10/44* | (2022.01) |
| *G06V 10/56* | (2022.01) |

(Continued)

(52) U.S. Cl.
CPC ....... *G01N 21/78* (2013.01); *G01N 33/54373* (2013.01); *G01N 33/743* (2013.01); *G01N 33/76* (2013.01); *G06T 11/206* (2013.01); *G06V 10/44* (2022.01); *G06V 10/56* (2022.01); *G06V 20/00* (2022.01); *G06V 20/52* (2022.01); *G01N 2021/7759* (2013.01); *G06T 2210/41* (2013.01)

(58) Field of Classification Search
CPC ............. G01N 21/78; G01N 33/54373; G01N 33/743; G01N 33/76; G01N 2021/7759; G01N 33/54388; G01N 21/8483; G06T 11/206; G06T 2210/41; G06V 10/44; G06V 10/56; G06V 20/00; G06V 20/52; G06V 2201/034; G06V 2201/10

See application file for complete search history.

(56) References Cited

U.S. PATENT DOCUMENTS

| | | | |
|---|---|---|---|
| 2016/0080548 A1* | 3/2016 | Erickson | G01N 21/8483 382/128 |
| 2021/0285946 A1* | 9/2021 | Lin | B01L 3/50273 |

OTHER PUBLICATIONS

Wong JXH, Liu FSF, Yu HZ. 2014. "Mobile app-based quantitative scanometric analysis". Anal. Chem. 86, pp. 11966-11971. (Year: 2014).*

* cited by examiner

Primary Examiner — Said Broome
Assistant Examiner — Andrew Shin
(74) Attorney, Agent, or Firm — K&L Gates LLP

(57) ABSTRACT

Systems, methods, and apparatus are disclosed for determining quantitative hormone and chemical analyte results from qualitative test results. An image is taken of an ovulation test device. The image is analyzed to identify a darkness intensity ratio (T/C ratio) between a darkness value of a test-line to a darkness value of a control-line. Additionally, a quantitative substance level may be determined using the T/C ratio, by identifying the type of test device and referencing a data structure that relates quantitative substance levels to T/C ratios for the identified type of test device.

24 Claims, 14 Drawing Sheets

Related U.S. Application Data

(60) Provisional application No. 63/033,767, filed on Jun. 2, 2020.

(51) Int. Cl.
*G06V 20/52* (2022.01)
*G06V 20/00* (2022.01)
*G01N 21/77* (2006.01)

| T/C Ratio to LH Level Mapping | |
|---|---|
| T/C Ratio Range | LH level |
| ≤0.2 | 3 |
| 0.2 < ratio≤0.3 | 5 |
| 0.3 < ratio≤0.45 | 7 |
| 0.45 < ratio≤0.6 | 10 |
| 0.6 < ratio≤0.7 | 13 |
| 0.7 < ratio≤0.8 | 15 |
| 0.8 < ratio≤0.9 | 17 |
| 0.9 < ratio≤1 | 20 |
| 1 < ratio≤1.1 | 22 |
| 1.2 < ratio≤1.3 | 25 |
| 1.3 < ratio≤1.4 | 30 |
| 1.4 < ratio≤1.5 | 40 |
| 1.5 < ratio≤1.7 | 50 |
| 1.7 < ratio≤1.8 | 65 |
| 1.8 < ratio≤2 | 80 |
| ≥2 | 80 |

FIG. 2

| Ratio | LH level | Rules of showing colors & Low/High/Peak |
|---|---|---|
| 0.1-1.5 | 2.5 | LH level ≤10, white, Low |
| 0.1-0.15 | 3.5 | |
| 0.15-0.2 | 5 | |
| 0.2-0.25 | 7.5 | |
| 0.25-0.3 | 10 | |
| 0.3-0.35 | 12.5 | LH level > 10, pink, High<br>When it's judged to LH peak,<br>change to deep purple.<br>When the LH level goes down, the<br>biggest LH level will be labeled as Peak. |
| 0.35-0.4 | 15 | |
| 0.4-0.45 | 17.5 | |
| 0.45-0.5 | 20 | |
| 0.5-0.55 | 22.5 | |
| 0.55-0.6 | 25 | |
| 0.6-0.65 | 27.5 | |
| 0.65-0.7 | 30 | |
| 0.7-0.72 | 32.5 | |
| 0.72-0.75 | 35 | |
| 0.75-0.77 | 37.5 | |
| 0.77-0.8 | 40 | |
| 0.8-0.82 | 42.5 | |
| 0.82-0.85 | 45 | |
| 0.85-0.87 | 50 | |
| 0.87-0.9 | 55 | |
| 0.9-0.92 | 60 | |
| 0.92-0.95 | 65 | |
| 0.95-0.97 | 70 | |
| 0.97-1 | 75 | |
| >1 | 80 | |

FIG. 3

QUANTITATIVE HORMONE AND CHEMICAL ANALYTE TEST RESULT SYSTEMS AND METHODS

PRIORITY CLAIM

This application comprises a continuation application of U.S. application Ser. No. 17/337,068 filed Jun. 2, 2021, which claims priority to and the benefit of U.S. Provisional Patent Application Ser. No. 63/033,767, filed on Jun. 2, 2020, the entire disclosure of which is hereby incorporated by reference.

TECHNICAL FIELD

The present subject matter relates generally to deriving reliable quantitative results from qualitative hormone and chemical analyte tests. Specifically, the present systems and methods provide a quantitative T/C ratio defined as a ratio of color density between a test-line (T-line) and a control-line (C-line) of a hormone and chemical analyte test. The T/C ratio is a reliable quantitative measurement used for subsequent analysis and recommendations. In addition, the quantitative T/C ratio can be reliably translated into the potentially more valuable quantitative hormone or chemical concentration level in the samples without additional hardware device or accessory.

BACKGROUND

There are numerous forms of rapid lateral flow immunoassay tests used for the detection of hormones, metabolite, and chemical substances in body fluids (e.g., urine, saliva, blood, etc.). These tests are valuable and widely used because they are cost effective, provide quick results, and generally more convenient than tests requiring blood to be drawn or testing using more complicated devices. The convenience of being able to take these minimally invasive tests in a self-directed, at home environment is a very valuable selling point for many users. However, the qualitative test results and the difficulty in tracking test results over time limit the effectiveness of the standard rapid lateral flow immunoassay tests.

In a typical rapid lateral flow immunoassay test, a test strip or other test device is brought into contact with the body fluid that is being analyzed. The body fluid causes a reaction that produces color bands to appear on the device for visual/qualitative analysis, including a control-line and a test-line. Typically, a user reads the test results by simply looking at the test results and comparing the color of the test-line against the color of the control-line. This qualitative analysis is problematic for many reasons. Most critically, it provides limited accuracy due to human error in making the visual comparison. In addition, it is difficult to track progress and show personalized patterns of test results without a reliable quantitative result.

As a practical example, there are many known home-use, ovulation test devices designed to provide users with their fertility status. Such devices include test strips and test cassettes that measure a concentration level of one or more analytes or hormones in a user's urine, saliva or blood sample. The one or more analytes may include estradiol and metabolites thereof (e.g., estrone-3-glucuronide, the urinary metabolite of progesterone). The one or more hormones may include luteinizing hormones ("LHs"), human chorionic gonadotropin ("hCG"), follicle stimulating hormone (FSH), progesterone, estrogen, estriol ("E3"), etc.

The known devices typically display one or more colored lines that represent a measured concentration or level of one or more analytes or hormones. For instance, the known devices provide a test-line (T-line) and a control-line (C-line). Many devices show a colored T-line and a colored C-line to represent whether a user's LH concentration in a urine sample is above a cutoff threshold or level (e.g., indicative of a positive result that a user is ovulating). If a manufacturer calibrates the test devices correctly, the color shading/darkness of T-line and C-line should be about same when an LH concentration level is at the cutoff or threshold level for a positive test. Many manufacturers use an FDA recommended 25 mIU/mL as the cutoff or threshold level for a positive test indication.

Depending on a concentration level, both the T-line and C-line are shown in a shade (e.g., an intensity or "color density") of a particular color, such as purple, pink, or red. In a typical example, for low analyte/hormone concentrate levels (i.e., a negative test result), some T-lines appear as a lighter shade or color intensity. For high analyte/hormone concentrate levels (i.e., a positive test result), some T-lines appear as a darker shade or intensity. In some tests, the shading of the C-line is relatively constant between analyte/hormone concentrate levels (though it can vary some), while shading of the T-line changes significantly based on the analyte/hormone concentrate levels. However, in other tests, the color density of the control-line is lighter when there is a higher concentration of the LH hormone being tested and the color density of the control-line is darker when there is a lower concentration of the LH hormone being tested.

To determine a test result, a user visually compares a color intensity of the T-line to a color intensity of the C-line. A known issue is that users may have different perceptions of color, shading, and/or intensity, which makes interpreting test results more difficult. Another issue is that the lighting conditions can make visual qualitative test results more difficult to analyze. For example, there are known systems that use cameras to capture images of T-lines and analyze the T-line in the image to determine the result. However, these systems typically struggle to provide consistent results unless the ambient lighting conditions are controlled, which can be difficult and/or require specialized hardware. In addition, systems that read test results through analysis of the T-line are not always able to accurately read/interpret test results that do not include a constant control-line. Further, known tests provide an "at the moment" positive or negative result. Such information does not indicate whether a user's ovulation window is opening or closing without conducting tests on subsequent days and tracking a comparison of the test results over time. Comparing qualitative test results over time is particularly difficult.

Accordingly, there is a need for systems and methods for producing reliable quantitative test results from the qualitative test results provided by the widely used inexpensive and convenient home-use tests without special designed or customized additional accessories or equipment. Reliable quantitative test results will greatly aid users in gaining more accurate results that may be used to monitor, track, and graph the progression of the test results over time, providing more thorough analysis enabling even greater insight into the characteristic being tested.

SUMMARY

To meet the needs described above, the present subject matter provides systems and methods that derive a quantitative T/C ratio (defined as a ratio of color density between a test-line (T-line) and a control-line (C-line) of a hormone and chemical analyte test) from the qualitative results of a typical rapid lateral flow immunoassay test or other qualitative test device that produce the visually identifiable control line and test line and test results are determined by the color density of the test line or color density relative to the control line. The resulting T/C ratio is a reliable quantitative measurement used for more accurate interpretation of the rest results, as well as for subsequent analysis and recommendations based on tracking test results over time. In addition, the quantitative T/C ratio can be reliably translated into the potentially more valuable quantitative hormone or chemical concentration level in the samples without additional hardware device or accessory.

Although the systems and methods taught herein apply to a wide range of rapid lateral flow immunoassay tests, to provide a clear example of an intended use case, the main examples used in this disclosure relate to systems, methods, and apparatus for providing quantitative hormone and chemical analyte tests results for the purposes of ovulation detection. Those having ordinary skill in the art will understand how the examples provided herein are applicable to any comparable rapid lateral flow immunoassay test, as well as other testing procedures whose results are provided through a qualitative comparison of the color density between a test-line and a control-line.

Further, it is important to note, although the primary embodiments described herein the test results are provided by a comparison of a single test-line and a single control-line, the advantages taught herein apply to systems and methods in which the test device provides two or more test-lines for comparison to a one or more control-lines. Alternatively, the advantages taught herein apply to systems and methods in which the test device provides two or more control-lines for comparison to one or more test-lines.

In one example, the systems, methods, and apparatus described herein provide quantitative test results derived from an analysis of the qualitative test results provided by standard home use ovulation tests. In a first step, the systems, methods, and apparatus detect both a T-line and a C-line in a digital image of the qualitative results from an ovulation test device. The systems, methods, and apparatus use one or more color models to determine a color intensity of each of the T-line and the C-line. The ratio of the T-line intensity relative to the C-line intensity is a quantitative measurement described herein as the T/C ratio. This process provides reliable and useful quantitative test results from otherwise qualitative testing devices. By using a comparison of the T-line and C-line color densities, the systems and methods taught herein control for ambient lighting conditions. In other words, because the systems and method rely on a comparison of the T-line to the C-line, rather than an independent analysis of the T-line, or a comparison of the T-line to a neutral background, consistent and reliable test results can be produced, regardless of ambient interference and lighting conditions.

By design, the color density of the C-line for many LH tests is not consistent between tested urine samples. For example, for test samples in which the LH hormone is detected at a higher level (compared to tested urine samples in which the LH hormone is detected at a lower level), the color density of the T-line becomes darker and the color density of the control-line becomes lighter. In these designs, the magnitude of the color density change for the T-line may be relatively small, but the comparative color densities of the T-line and C-line may be capable of representing a wider range of test results. Despite the different types of LH tests (e.g., consistent C-line tests, inconsistent C-line tests), using the T/C ratio to quantize the test results, allows the systems and methods described herein to handle a wide range of tests, whether they include a more or less consistently dense C-line.

In some examples, the systems, methods, and apparatus then compare the T/C ratio to a data structure that relates T/C ratios to quantitative hormone levels for different types of ovulation test devices. Based on this comparison, the systems, methods, and apparatus can be used to determine a quantitative hormone level that corresponds to the determined ratio. The systems, methods, and apparatus can be configured to display the quantitative hormone level to a user, as well as an indication as to whether the quantitative hormone level is at a peak or at a low. Such information provides a user with easy to understand results regarding whether she is ovulating and whether she will have a high probability of getting pregnant if she has intercourse. While the derivation of a hormone level or other end result may be useful in some situations, it is important to note that a primary benefit of the present subject matter is simply the ability to generate a reliable and trackable quantitative result from an otherwise qualitative test result.

As discussed herein, there are many different types of conventional ovulation test devices for detecting ovulation including test strips, midstream tests, and cassettes. The example systems, methods, and apparatus are configured to determine which type of ovulation test device is being used based on the recorded image. The systems, methods, and apparatus may use a color, pattern, and/or text marking on a handle to determine a brand and/or type of ovulation test device. The systems, methods, and apparatus may also use a C-line and/or T-line spacing or color to determine a brand and/or type of ovulation test device. In other words, the systems and methods provided herein can identify the brand of test and use historical data related to the branded test to translate the T/C ratio into a hormone level or other derived value. Accordingly, the systems, methods, and apparatus can thereby enable a user to determine their hormone level for ovulation regardless of which type of ovulation test device is used.

As a key feature, the digitization of a user's T/C ratio enables the systems, methods, and apparatus to provide tracking, trending, and prediction derived from subsequent test results over a period of time. For instance, the systems, methods, and apparatus may aggregate a user's measured T/C ratio over menstrual cycles or months to show how the user's hormone levels change and provide an indication of a peak ovulation time period. The systems, methods, and apparatus may use these trends to predict a peak ovulation time period for subsequent next menstrual cycles or months. This prediction provides a user a possible high fertility window and peak fertility date (based on trending T/C ratios) without having to conduct frequent (or any) ovulation tests.

Converting a user's T/C ratio into the quantitative hormone level, as described further herein, enables the systems, methods, and apparatus to provide analysis, tracking, trending, and predictions based on hormone levels derived from subsequent test results over a period of time. For instance, the systems, methods, and apparatus may aggregate a user's LH hormone level over several menstrual cycles or months to show how the user's hormone levels change and use the data to provide an indication of a peak ovulation time period. The systems, methods, and apparatus may use these trends to predict a peak ovulation time period for subsequent menstrual cycles or months. These predictions provide a user the likely peak hormone level data without having to conduct frequent (or any) ovulation tests. The hormone level can also correlate with other fertility symptoms or indications, such as follicle size or progesterone blood test results. Accordingly, both the T/C ratio, and the quantitative hormone level to which it may be translated, can be very valuable to users.

As described herein, translating qualitative test results into a quantitative T/C ratio enables easier and more reliable tracking of test results over time, which can enable further personalization of test results. With respect to the ovulation example used herein, it is common for different people to have different peak hormone levels during their ovulation time period. By tracking a quantitative test result over time, it is easier to provide a test result that is a comparison to the user's current T/C ratio to the user's historical T/C ratios to provide even more accurate and valuable personalized test results.

For example, the systems, methods, and apparatus can provide further user personalization by adjusting a threshold between a positive/high and negative/low results based on prior peak hormone levels for a user. For example, for a user that has a relatively low peak hormone level (e.g., a peak hormone level less than 25 mIU/mL or a hormone level corresponding to a T-line/C-line color intensity ratio less than 0.8), the systems, methods, and apparatus can be configured to reduce the threshold for returning a positive/high result.

In some embodiments, the systems, methods, and apparatus are embodied on an application operating on a user device (e.g., a smartphone or tablet computer) and/or a server connected to the application. As disclosed herein, the application is configured to record an image of an ovulation test device. The application is configured to ensure the recorded image includes a test area with a colored T-line and a colored C-line. The application may also ensure a handle or other identifying marking on the ovulation test device is also included within the image. The application may provide one or more prompts or alignment markings (provided around the C-line and the T-line) to help a user position and/or focus a camera of the user device to record the image. In some instances, the application selects an image from a stream of images that clearly shows the test area of the ovulation test device. The application may prompt a user to retake an image if none of the received images clearly shows the test area.

The application is configured to transmit the recorded image to a communicatively coupled server. The example server analyzes the image to identify the test area and/or a handle. In some instances, the server (or the application) crops the image around the ovulation test device to remove unnecessary background features. The server uses the identification of the handle and/or identification of an identified position and/or color of the T-line and the C-line in the test area to determine a type of the ovulation test device. Further, the server determines a color intensity of the T-line and the C-line and calculates a corresponding color intensity ratio. In some embodiments, the server is configured to convert the T-line and the C-line to grayscale, determine a darkness value, and calculate the color intensity ratio using the T-line and C-line darkness values.

In some embodiments, the server compares the determined color intensity ratio and the type of the ovulation test device to a data structure that relates quantitative hormone levels to color intensity ratios for different types of ovulation test devices. The server determines a quantitative hormone level for the user based on the comparison. The server transmits the quantitative hormone level and/or the corresponding color intensity ratio to the application for display in a user interface on a screen of the user device. In some embodiments, the server and/or the application determines if the quantitative hormone level and/or the corresponding color intensity ratio exceed a threshold. If the threshold is exceeded, the server and/or the application show the quantitative hormone level and/or the corresponding color intensity ratio as a positive/high result. If the threshold is not exceeded, the server and/or the application show the quantitative hormone level and/or the corresponding color intensity ratio as a negative/low result. If the hormone level reaches a high point and then starts to decline, the previous high point in the hormone level will be marked as a peak level.

The application is configured to display additional user interfaces that show quantitative hormone levels and/or the corresponding color intensity ratios for a user over a calendar month and/or menstrual cycle. The quantitative hormone levels and/or the corresponding color intensity ratios may be displayed as color-coded numerical values in conjunction with corresponding images (or cropped image) of the recorded ovulation test device. The quantitative hormone levels and/or the corresponding color intensity ratios may also be displayed in a graph to show a peak hormone level, which may be used by the application or the server to predict future peak hormone levels for subsequent months or menstrual cycles.

In light of the disclosure set forth herein, and without limiting the disclosure in any way, in a first aspect of the present disclosure, which may be combined with any other aspect, or portion thereof, described herein In a primary embodiment, a testing system includes: a test device that including a visually identifiable test line and a visually identifiable control line formed in response to exposure to a tested substance; and a user device including a camera, a processor, a display, and memory storing program instructions, wherein, in response to executing the program instructions, the processor: receives an image of the test device from the camera, the image including a visually identifiable test-line and a visually identifiable control-line; determines a test-line value defined as a numerical value of a color density of the test-line in the image; determines a control-line value defined as a numerical value of a color density of the control-line in the image; calculates a T/C ratio defined as the relative value of the test-line value to the control-line value.

In another embodiment, a testing system further includes: wherein, in response to executing the program instructions, the processor further: determines a second test-line value defined as a numerical value of a color density of a second test-line in the image; and calculates a T/C ratio defined as the relative value of the second test-line value to the control-line value.

In some embodiments, the test device is a rapid lateral flow immunoassay test device. The test device many be any one of an ovulation, pregnancy, progesterone, estrogen, estriol, and follicle-stimulating hormone test device. The tested substance may be one of urine, blood, and saliva.

In response to executing the program instructions, the processor may select the image from a stream of images received from the camera. The image may include a visually identifiable portion of the test device, further wherein, in response to executing the program instructions, the processor identifies a model of the test device based on the visually identifiable portion of the test device. The processor identifies the test-line and the control-line by identifying a location, edges, and line width within a test area that corresponds to a defined test-line and a defined control-line for the identified model of the test device.

In some embodiments, the processor determines the color density of the test-line and the color density of the control-line using a color model that represents color density with a numeric value.

In some embodiments, in response to executing the program instructions, the processor further: compares the T/C ratio for a user for a plurality of days during at least one complete menstrual cycle; determines a peak T/C ratio for the menstrual cycle; and presents information indicative of the peak T/C ratio through the display. The information indicative of the peak T/C ratio may include a calendar including information indicative of an ovulation cycle of the user in the future.

In some embodiments, the memory stores a data structure that relates T/C ratio to quantitative levels of a substance being tested. The characteristic being tested may be the presence of one or more of a luteinizing hormone, a human chorionic gonadotropin, progesterone, estrogen, estriol, and a follicle-stimulating hormone in the tested substance. The T/C ratio may be translated into a quantitative level of a substance. Further, in response to executing the program instructions, the processor may further: compare the hormone level for a user for a plurality of days including at least one complete menstrual cycle; determine a peak hormone level for the menstrual cycle; and present information indicative of a comparison between a measured hormone level and the peak hormone level through the display.

In another embodiment, the testing system includes: a test device that, in response to exposure to a tested substance, provides a visually identifiable test line and a visually identifiable control line; a camera, including an image capture mechanism and a camera communication interface; a processor, including an image processing mechanism and a processor communication interface in communication with the camera communication interface; and a display controlled by the processor; wherein, when in use: the test device is exposed to the tested substance to provide the visually identifiable test line and the visually identifiable control line; the camera captures one or more images, each image including the visually identifiable test line and the visually identifiable control line; the processor receives the one or more images from the camera; the processor determines a test line value defined as a numerical value of a color density of the test line in the one or more images and a control line value defined as a numerical value of a color density of the control line in the one or more images; and the processor calculates a T/C ratio defined as the relative value of the test line value to the control line value.

In another aspect, any of the features, functionality and alternatives described in connection with any one or more of FIGS. 1 to 9 may be combined with any of the features, functionality and alternatives described in connection with any other of FIGS. 1 to 9.

In light of the present disclosure and the above aspects, it is therefore an advantage of the present disclosure to provide more reliable and accurate hormone and/or analyte level results for qualitative test results.

Another advantage of the present disclosure to provide systems and method of improving the reliability of qualitative tests by providing accurate quantitative results, regardless of ambient light conditions.

It is another advantage of the present disclosure that the T/C ratio can read and produce the reliable quantitative results for a wide range of test types, including those that have consistently dense control-lines and those in which the color density of the control-lines are affected by the hormone level.

It is another advantage of the present disclosure to provide an easy to use mobile application for presenting additional data from a conventional hormone level test and tracking the quantitative results over time.

It is yet another advantage of the present disclosure to provide for the conversion of results from any type or brand of conventional hormone level test (including, but not limited to, strip tests, midstream tests, and cassette ovulation tests) to quantitative results.

It is also another advantage of the present disclosure to obtain the quantitative LH level at a point-of-collection without a user having to use additional expensive devices or take expensive and inconvenient lab tests.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE FIGURES

FIGS. 2 and 3 are diagrams of an example data structure that relates different color intensity ratios to quantitative hormone levels for different brands and/or types of ovulation test devices, according to example embodiments of the present disclosure.

DETAILED DESCRIPTION

Figure 1:
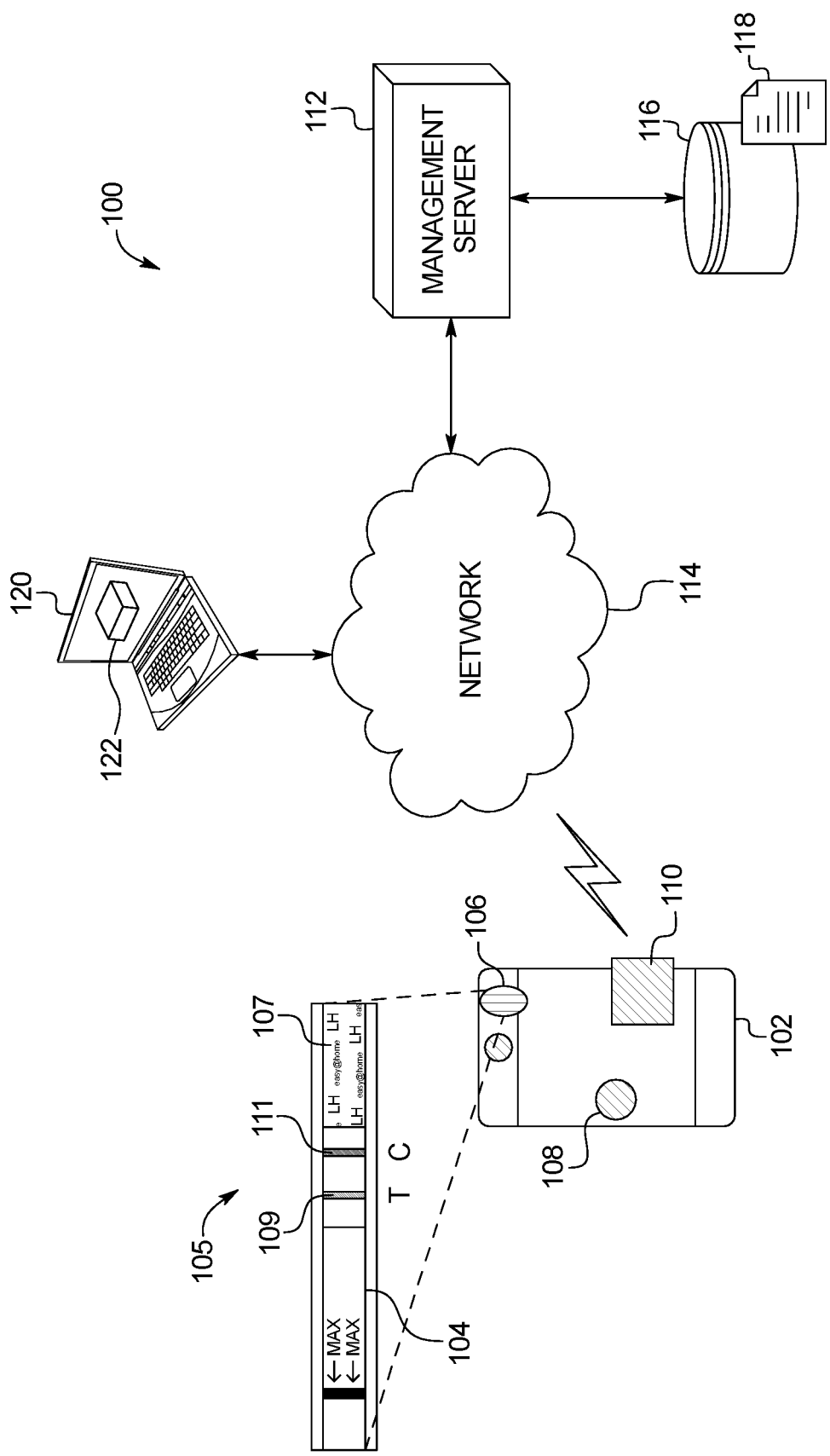
FIG. 1 is a diagram of a quantitative ovulation testing system, according to an example embodiment of the present disclosure.

As described above, the present subject matter provides systems and methods that derive a quantitative T/C ratio (defined as a ratio of color density between a test-line, T-line, and a control-line, C-line, of a hormone and chemical analyte test) from the qualitative results of a typical rapid lateral flow immunoassay test or other qualitative test device that produce the visually identifiable control-line and test-line and test results are determined by the color density of the test-line or color density relative to the control-line. The resulting T/C ratio is a reliable quantitative measurement used for more accurate interpretation of the rest results, as well as for subsequent analysis and recommendations based on tracking test results over time. In addition, the quantitative T/C ratio can be reliably translated into the potentially more valuable quantitative hormone or chemical concentration level in the samples without additional hardware device or accessory.

Although the systems and methods taught herein apply to a wide range of rapid lateral flow immunoassay tests, to provide a clear example of an intended use case, the main examples used in this disclosure relate to systems, methods, and apparatus for providing quantitative hormone and chemical analyte tests results for the purposes of ovulation detection. Those having ordinary skill in the art will understand how the examples provided herein are applicable to any comparable rapid lateral flow immunoassay test, as well as other testing procedures whose results are provided through a qualitative comparison of the color density between a test-line and a control-line.

The following examples teach how to digitize results of a home ovulation test device to provide quantitative hormone and/or chemical analyte information to a user. The systems, methods, and apparatus in the examples provided are configured to analyze one or more images of an ovulation test device to determine a color intensity ratio between a T-line and a C-line. The systems, methods, and apparatus compare the determined color intensity ratio to a data structure that relates different color intensity ratio to hormone levels for different types and/or brands of ovulation test device. This configuration enables the systems, methods, and apparatus to provide quantitative hormone and chemical analyte tests results for virtually any commercially available ovulation test device without any change in procedure for a user and without any additional accessory or equipment needed.

As disclosed herein, the systems, methods, and apparatus enable the tracking of a progression and/or trend of a user's hormone changes (e.g., ovulation hormones) over time. Periodic sampling of a user's hormone levels during the course of a menstrual cycle enables the systems, methods, and apparatus to create a personalized estimation as to a time period during which a user is likely to be at peak ovulation. The personalized estimation also identifies positive/high and negative/low hormone levels that are based on a user's previous hormone trends instead of population averages, which may overestimate positive/high threshold levels for some users that have relatively low levels of ovulation hormones.

Reference is made herein to determining concentration levels of luteinizing hormones ("LHs"). However, it should be appreciated that the systems, methods, and apparatus may be used to determine concentration levels of one or more analytes, including human chorionic gonadotropin (hCG), follicle-stimulating hormone (FSH), progesterone or its metabolites, estradiol and metabolites thereof (e.g., estrone-3-glucuronide), etc. Further, reference is made herein to placing the ovulation test device in urine. In other embodiments, the systems, methods, and apparatus may be used for blood tests (e.g., serum tests), saliva tests, or any other bodily fluid.

Reference is also made herein to operations performed by an application operating on a user device and operations performed by a server. It should be appreciated that in other embodiments, most, if not all, of the operations may be performed by the application. Alternatively, most, if not all, of the operations may be performed by the server.

Quantitative Ovulation Testing System Embodiment

FIG. 1 is a diagram of a of a quantitative ovulation testing system 100, according to an example embodiment of the present disclosure. The example quantitative ovulation testing system 100 includes a user device 102 configured to record images of an ovulation test device 104 and display one or more user interfaces indicative of a user's quantitative T/C ratio or hormone level. The example user device 102 may include a smartphone, cellular phone, tablet computer, laptop computer, personal computer, workstation, smartwatch, smart-eyewear, etc. While FIG. 1 shows only a single user device 102, it should be appreciated that the system 100 may include additional user devices. For example, the management server 112 may be in communication with any number of user devices for graphing, calculating, trending and/or predicting the ovulation date and fertile window based on the calculated T/C ratio or hormone level.

The ovulation test device 104 includes a test area 105 and a handle 107. The test area 105 includes a T-line 109 and a C-line 111. The T-line 109 is configured to change a color after a user has caused the test device 104 to contact urine. A color of the T-line 109 is indicative of a hormone level, with darker colors corresponding to higher hormone levels. The C-line 111 is to provide a color comparison for the T-line. As noted above, the color density of the control-line for many LH tests may be consistent regardless of the level of hormone present in the tested substance. In other LH tests, the color density of the control-line may vary depending on the level of LH present in the tested substance. For example, in some tests, when the LH hormone level rises in the urine sample, the color density of the test-line is darker and, when the LH hormone level drops in the urine sample, the color density of the control-line becomes lighter.

Currently, users have to visually compare the T-line 109 to the C-line 111 to estimate the color difference between the two lines, which they then use to estimate whether the LH hormone level is high or low, which is used to predict whether they are ovulating. This can be especially hard for users with certain color blindness or other visual imparities. Also, different lighting conditions or backgrounds may influence users' judgement and make interpreting the results more difficult. Additionally, this comparison provides only a single data point and does not provide indications of future or past hormone levels, and does not provide any indication as to whether a user is at peak ovulation. The system 100 disclosed herein uses colors of the C-line 109 and the T-line 111 to determine a quantitative hormone for a user, which is display via the user device 102.

To record images of the ovulation test device 104, the user device 102 includes a camera 106. The camera 106 may include any imaging device configured to record an image or a stream of images. The camera 106 may be located on a front face and/or rear face of the user device 102. In other embodiments, the user device 102 may be separate from and communicatively coupled to the camera 106 via, for example, a USB® connection, a Bluetooth® connection, a Lightning® connection, an NFC connection, etc.

The example user device 102 of FIG. 1 includes an application 108 and a processor 110. The application 108 is defined by, or specified by, one or more machine-readable instructions stored in a memory device of the user device 102. The instructions may specify one or more algorithms, routines, or operations performed by the application 108. The instructions may also specify one or more user interfaces for display on a screen of the user device 102. The processor 110 executes the instructions to provide for operation of the application 108. Disclosure herein to the application 108 performing certain operations refers to the instructions executed by the processor 110 to enable the operations to be carried out on the user device 102. The application 108 may include a stand-alone software application (e.g., an app), a web browser, or a plug-in for a web browser. In some embodiments, the application 108 may operate without connecting to a server or a network.

The example system 100 of FIG. 1 includes a management server 112 that is connected to the user device 102 via a network 114. The network 114 may include any wired and/or wireless network including the Internet, an Ethernet, a cellular network, or combinations thereof. The management server 112 may include a processor, a group of processors, a controller, a microcontroller, a database etc. for receiving/storing data, performing computations, and outputting data.

As described herein, the server 112 is configured to receive one or more images from the user device 102 of the ovulation test device 104. The server 112 analyzes the image to identify a type and/or brand of the ovulation test device 104. The server 112 may use a color or spacing of the T-line 109 and/or the C-line 111 to determine a type and/or brand of the ovulation test device 104. Additionally or alternatively, the server 112 may identify markings or other indicia on the handle 107, which are used to determine the type and/or brand of the ovulation test device 104.

In a key aspect of the systems and methods provided herein, the server 112 calculates a T/C ratio based on the ratio of a T-line 109 value compared to a C-line 111 value. The values of the T-line 109 and C-line 111 are based on the color density (i.e., color intensity or color darkness) of the T-line 109 and C-line 111. The server 112 may determine a color and/or color intensity of the T-line 109 and the C-line 111 using at least one of a red, green, and blue ("RGB") color model, or a cyan, magenta, yellow, and key ("CMYK") color model, a cyan, light cyan, magenta, light magenta, yellow, and key ("CcMmYK") color model or other color model that can represent the color density with a numeric value. The server 112 may use a determined color of the T-line 109 and the C-line 111 to identify the type and/or brand of the ovulation test device 104.

The server 112 may use the color intensity to determine a color intensity ratio between the T-line 109 and the C-line 111. In one example, the server 112 converts an image to grayscale using the color intensity. The server 112 then analyzes the grayscale values in the image to calculate darkness values of the T-line 109 and the C-line 111. The server 112 determines a color intensity ratio as a ratio of a darkness value of the T-line 109 to a darkness value of the C-line 111.

The server 112 is communicatively coupled to a memory device 116, which stores a data structure 118 that relates different color intensity ratios to quantitative hormone levels for different brands and/or types of ovulation test devices 104. The memory device 116 may include any hard disk drive, solid state drive, flash memory, distributed storage system, etc. for storing and managing data. The server 112 uses the determined brand and/or type of the ovulation test device 104 and the determined color intensity ratio to determine a corresponding quantitative hormone level. The server 112 transmits the quantitative hormone level to the user device 102 via the network 114 for display by the application 108.

FIGS. 2 and 3 are diagrams of example data structures 118 that relates different color intensity ratios to quantitative hormone levels for different brands and/or types of ovulation test devices 104, according to example embodiments of the present disclosure. FIG. 2 shows a first table or file 118a of the data structure 118 for a first type of ovulation test device 104. FIG. 3 shows a second table or file 118b of the data structure 118 for a second type of ovulation test device 104. As shown in FIG. 2, a color intensity ratio ("T/C Ratio Range") is between 0.2 to 2.0 for the first type of ovulation test device 104, which corresponds to a hormone level range between 3 mIU/mL to 80 mIU/mL. The ovulation test device 104 corresponding to the table 118a of FIG. 2 may represent a conventional test strip or test cassette where the T-line may be as dark or darker than the C-line after 25 mIU/mL. As a result, the color intensity ratios may be greater than 1.0.

FIG. 3 shows that for the second type of ovulation test device 104, the color intensity ratio ranges from 0.1 to 1, which corresponds to a hormone level range between 2.5 mIU/mL to 80 mIU/mL. The ovulation test device 104 is manufactured by the Assignee of the subject application and is configured to have a very stable and dark C-line that corresponds to a hormone level 80 mIU/mL. As a result, the T-line, at a maximum, will be no darker than the C-line. Accordingly, the table 118b has a maximum color contrast ratio of 1.0.

FIGS. 2 and 3 illustrate that different types of ovulation test devices 104 have different color intensity ratios for the same LH levels, even when converted to grayscale. Accordingly, the data structure 118 of the memory device 116 is configured to store a table or file for each type and/or brand of ovulation test device. In some embodiments, the server 112 is configured to calibrate large data sets in order to map color intensity ratios to hormone levels. For example, the server 112 may produce and/or access big data associated with branded LH tests to correlate the test images using urine samples with different standardized LH concentrations. The server 112 may conduct and/or access calibration tests using urine sample with standard LH concentrations including, but not limited to, 5 mIU/mL, 7 mIU/mL, 13 mIU/mL, 15 mIU/mL, 25 mIU/mL, 50 mIU/mL, 100 mIU/mL etc. The server 112 may produce a T/C color intensity reference ratio for each test image. The server 102 then records and maps (e.g., graph, tabulate, etc.) the correlation of T/C color intensity reference ratios and LH levels.

As shown in FIG. 3, in some embodiments, the table or file 118b of the data structure 118 includes one or more thresholds. The table 118b includes a threshold corresponding to a low/negative LH level and a condition corresponding to a peak LH level. The threshold and condition may be defaults that are modified by the server 112 and/or the application 108 after analyzing user hormone trends. The threshold corresponds to LH levels that are equal to and less than 10 mIU/mL. The server 112 is configured to designate or label quantitative hormone levels that are below this threshold as 'low' or 'negative'. The server 112 is configured to designate or label quantitative hormone levels that are greater than this threshold as 'high' or 'positive'. The condition corresponds to a peak condition, which may be detected by the server 112 based on a change in trend slope or identification of a local maximum LH level among LH levels designated as being 'high'.

The table 118b of FIG. 3 also specifies a graphical representation for the quantitative hormone levels. For example, quantitative hormone levels designated as being 'low' are to be displayed by the application 108 in a white background, while quantitative hormone levels designated as being 'high' are to be displayed by the application 108 in a pink background and a quantitative hormone level designated as being 'peak' is to be displayed by the application 108 in a purple background. It should be appreciated that the any type of graphical representation differentiation may be used between the low/high/peak designations and may include other colors, icons, text, graphics, etc.

Returning to FIG. 1, the system 100 may optionally include one or more clinician computers 120 operating a respective application 122. The clinician computer 120 is communicatively coupled to the user device 102 and/or the management server 112 via the network 114. The application 122 on the clinician computer 120 is configured to display a user's hormone trends to a registered clinician. The application 122 may be used by the clinician to transmit messages to the application 108 on the user device 102 and/or to analyze LH levels for a user to determine if a medical treatment or therapy is needed, such as a hormone injection to improve fertility.

User Device and Application Embodiment

Figure 4:
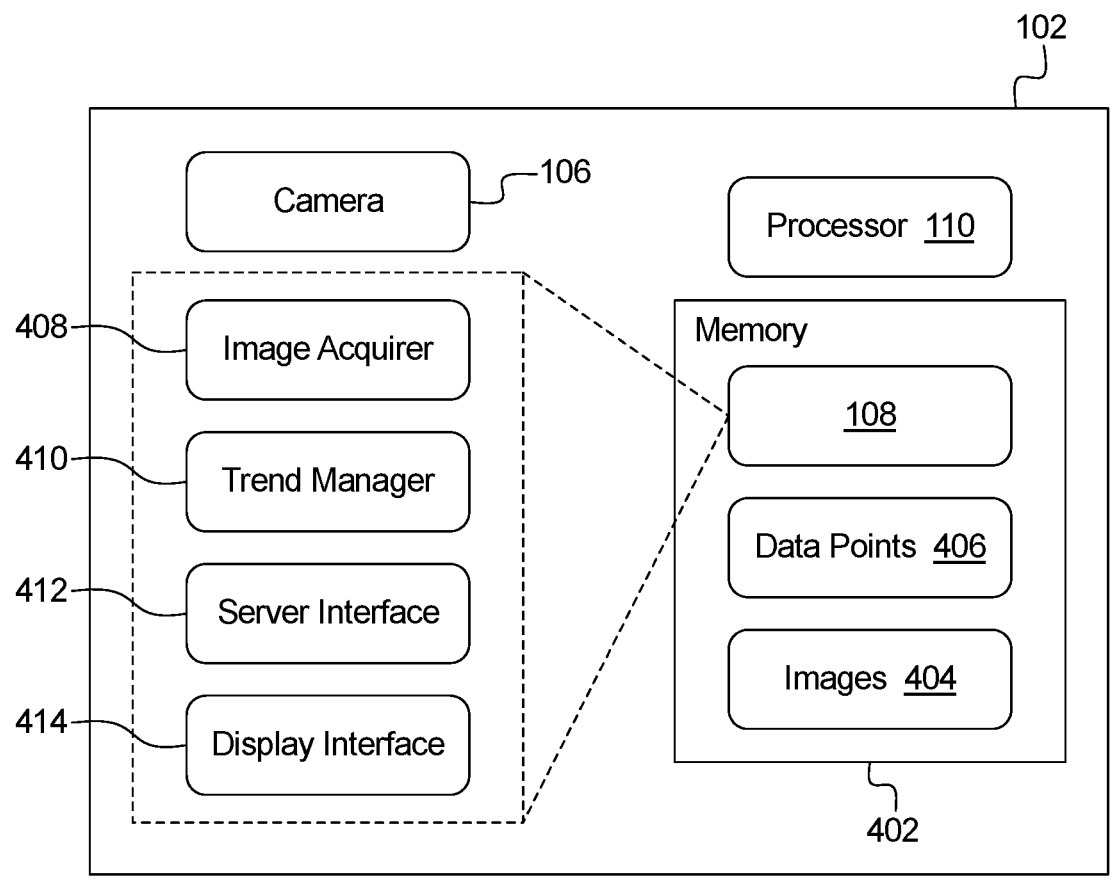
FIG. 4 is a diagram of a user device and an application of the quantitative ovulation testing system of FIG. 1, according to an example embodiment of the present disclosure.

FIG. 4 shows an example diagram of the user device 102, according to an example embodiment of the present disclosure. The user device 102 includes the processor 110 and a memory device 402 storing instructions defining the application 108. The processor 110 may include a microcontroller, a controller, an application specific integrated circuit ("ASIC"), a central processing unit included on one or more integrated circuits, etc. The memory 402 may include any volatile or non-volatile data/instruction storage device. The memory 402 may include, for example, flash memory, random-access memory ("RAM"), read-only memory ("ROM"), Electrically Erasable Programmable Read-Only Memory ("EEPROM"), etc.

The example memory device 402 is configured to store images 404 of the ovulation test device 104 recorded by the camera 106. The images 404 may be stored in any format including Portable Network Graphics ("PNG"), Joint Photographic Experts Group ("JPEG"), Graphics Interchange Format ("GIF"), etc. The processor 110 may apply a time and/or date stamp to each image 404 to preserve a record of when the ovulation test was performed. The processor 110 may also assign an identifier to each image 404.

The memory device 402 also stores data points 406 of quantitative hormone levels and/or color intensity ratios. In some embodiments, each data point 406 may also include a test result indication such as 'low' or 'negative' and/or a background color (e.g., white, pink, purple, etc.). Each data point 406 may be associated by the processor 110 to a corresponding image 404. For example, the processor 110 may associate or otherwise store a first data point 406 to an image 404 that was analyzed to generate the data point. This association enables the application 108 to display the images 404 adjacent to the data points 406.

As shown in FIG. 4, the application 108 includes operational modules including an image acquirer 408, a trend manager 410, a server interface 412, and a display interface 414. The example image acquirer 408 is configured to obtain one or more images of the ovulation test device 104. In some embodiments, the image acquirer 408 is configured to provide a number of options for acquiring an image including auto scan, manual select, and select an image from an album or gallery.

Figure 5:
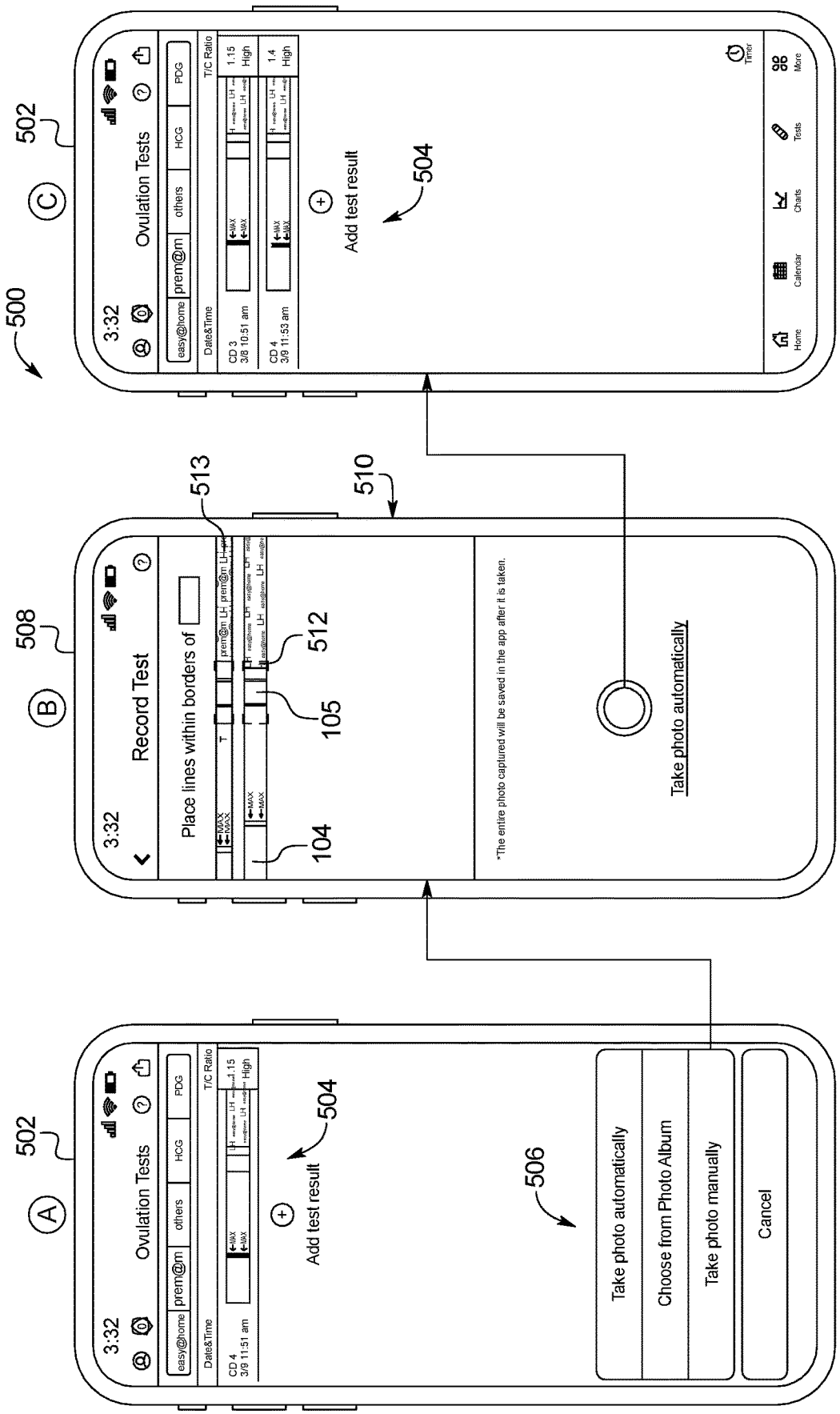
FIG. 5 is a diagram of a process flow provided by the application of the user device for manually acquiring an image, according to an example embodiment of the present disclosure.

FIG. 5 shows a process flow 500 provided by the image acquirer 408 of the application 108 for manually acquiring an image 404, according to an example embodiment of the present disclosure. At Event A, the image acquirer 408 cause the display interface 414 of the application 108 to display a user interface 502 prompting a user to select an image selection method via prompt 506. The user interface 502 also includes a results section 504 showing prior images 404 and corresponding data points 406. Specifically, the results section 504 of FIG. 5 related to Event A shows an image 404 recorded on 3/9 at 11:51 AM and a corresponding color intensity ratio (i.e., T/C ratio) of 1.4 (High). The results section 504 includes an icon to add a test result, selection of which causes the display interface 414 to show prompt 506.

At Event B, the image acquirer 408 causes the display interface 414 to display user interface 508, which includes image capture section 510. As shown in FIG. 5, the application 508 uses or integrates with a camera function of the user device 102 to show current images as recorded by the camera 106. The image acquirer 408 causes an alignment marker 512 to bracket the test area 105 of the ovulation test device 104. In some embodiments, the image acquirer 408 uses image recognition of the T-line and/or the C-line to determine where the alignment marker 512 is to be displayed. In other embodiments, the image acquirer 408 displays the alignment marker 512 as a template over a current image shown in the image capture section 510.

The image acquirer 408 also displays a sample image 513 overlaid the current image. The sample image 513 provides a visual example of how a user is to align the test area 105 within the alignment marker 512. In some embodiments, the image acquirer 408 determines a type or brand of the ovulation test device 104 within the image using a location of the test area 105, positioning, spacing, and/or colors of the T-line and/or C-line, and/or a color/text on a handle. The image acquirer 408 then selects a sample image 513 that corresponds to the determined type or brand of test device 104. In these embodiments, the image acquirer 408 may store the type or brand of the ovulation test device 104 to metadata of the acquired image 404.

After the user has determined that the test area 105 of the ovulation test device 104 is within the alignment marker 512, the user interface 508 includes an icon to enable an image to be recorded. Event C shows the user interface 502 with the recorded image from Event B. The recorded image 404 is stored by the image acquirer 408 to the memory device 402. In these examples, the image acquirer 408 may crop the image 404 to include at least a portion of the ovulation test device 104 including the test area 105 and the handle. The user interface 502 at Event C also shows a calculated quantitative T/C ratio, which is shown as a color intensity ratio of 1.4 (High). The quantitative hormone level may be determined by the application 108 and/or the server 112 of FIG. 1 by analyzing the T-line and the C-line in the test area 105. The displayed quantitative T/C ratio corresponds to a data point 406 stored in the memory device 402 and associated with the recorded image.

Figure 6:
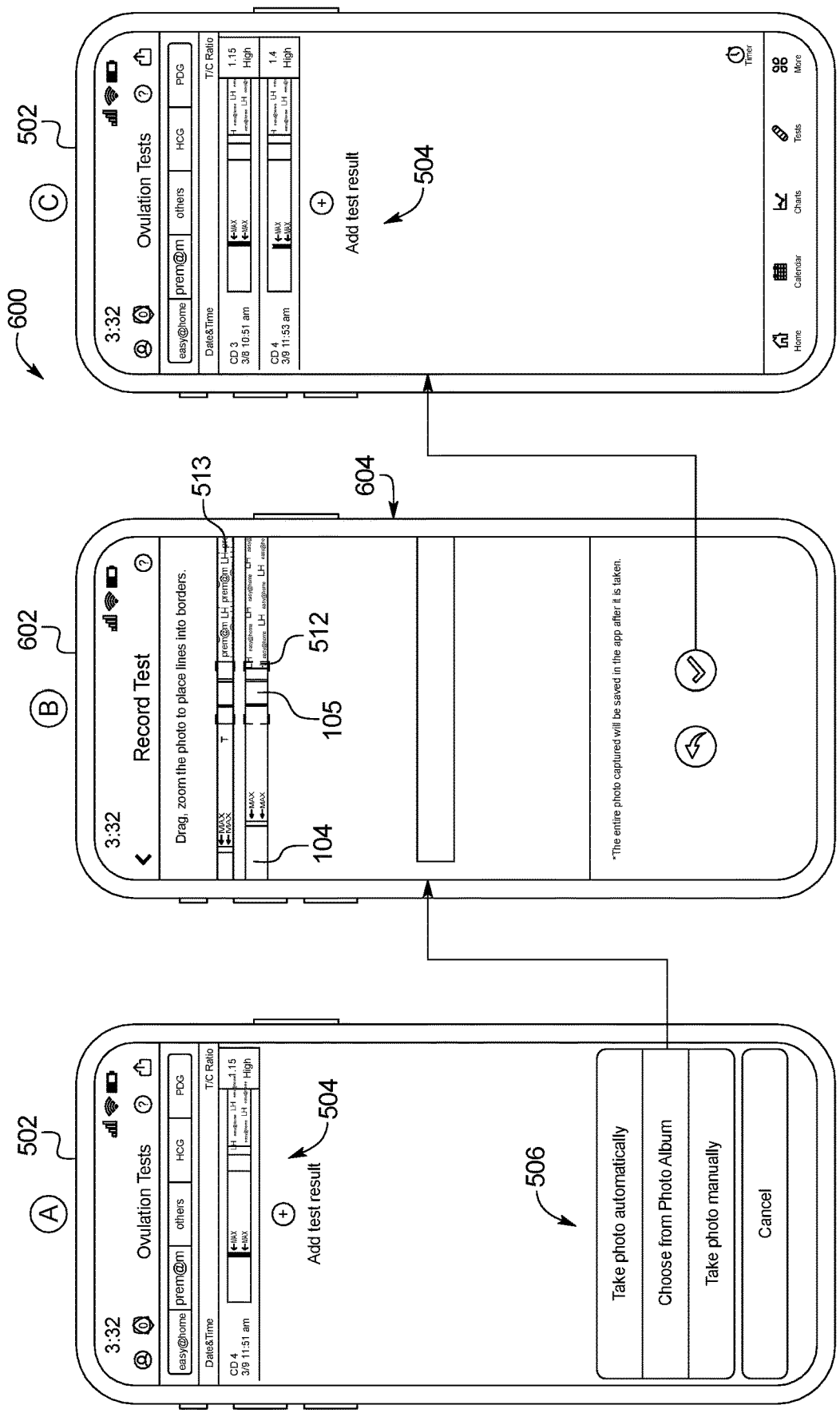
FIG. 6 is a diagram of a process flow provided by the application of the user device for selecting an image from a gallery or album, according to an example embodiment of the present disclosure.

FIG. 6 shows a process flow 600 provided by the image acquirer 408 of the application 108 for selecting an image 404 from a gallery or album, according to an example embodiment of the present disclosure. At Event A, the image acquirer 408 causes the display interface 414 of the application 108 to display the user interface 502 prompting a user to select an image selection method via the prompt 506. In this example, the user selects the "Choose from Photo Album" option. This selection causes the image acquirer 408 to display the user interface 602.

At Event B, a user views a photo album and selects an image. The image acquirer 408 causes the image to be displayed in an image alignment section 604. In this example, the image alignment section 604 includes the alignment brackets 512 and the sample image 513. The image alignment section 604 enables a user to move an image within the section such that the test area 105 is shown as being within the alignment brackets 512. After a user a properly positioned the image, the user interface 602 includes an icon to save the image, which is stored as an image 404 to the memory device 402. Similar to the process flow 500 of FIG. 5, the process flow 600 of FIG. 6 at Event C includes the application 508 and/or the server 112 analyzing the selected image 404 to determine a quantitative T/C ratio (e.g., data point 406). The determined quantitative T/C ratio is displayed adjacent to the image 404 in the results section 504 of the user interface 502.

Figure 7:
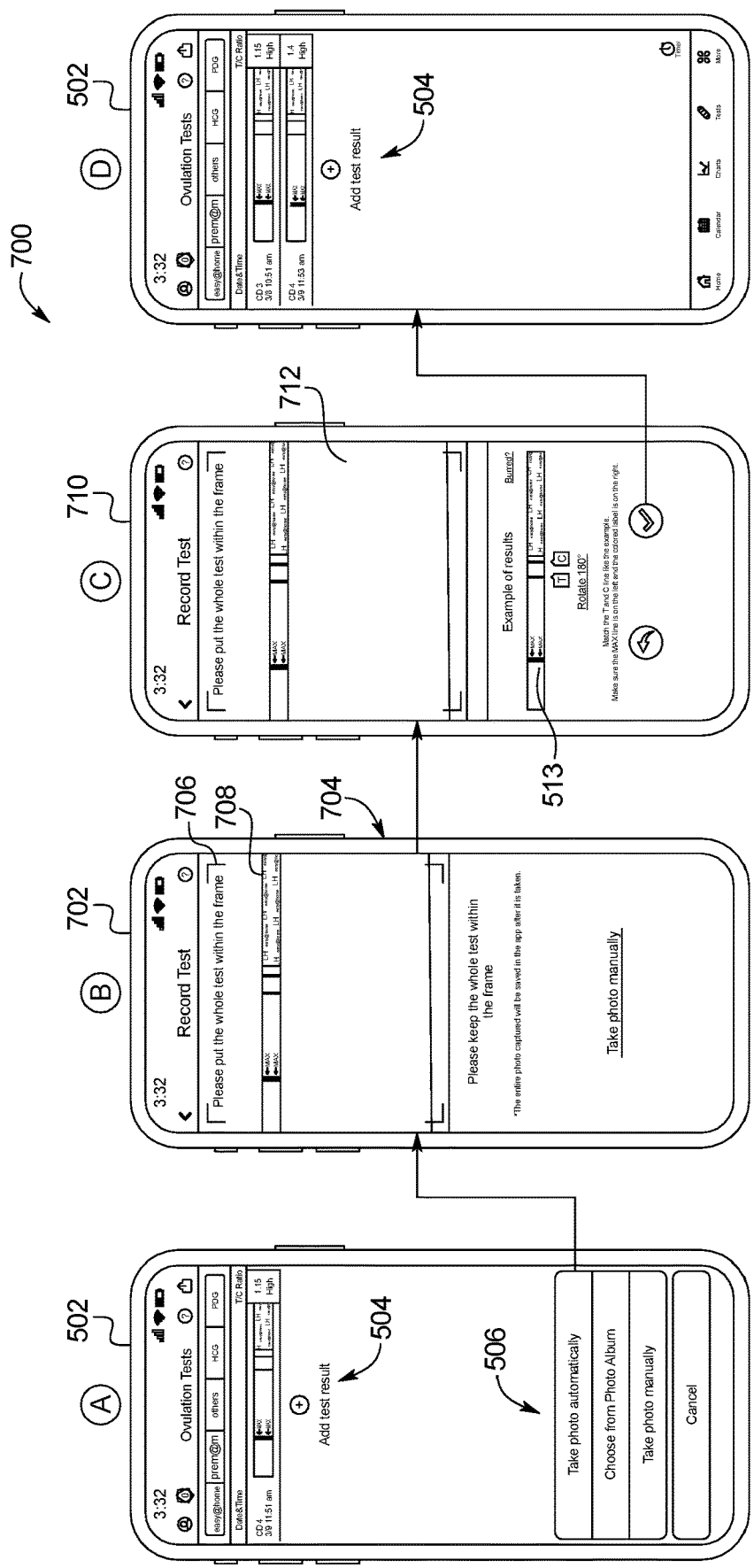
FIG. 7 is a diagram of a process flow provided by the application of the user device for selecting an image by automatically obtaining an image, according to an example embodiment of the present disclosure.

FIG. 7 shows a process flow 700 provided by the image acquirer 408 of the application 108 for selecting an image 404 by automatically obtaining an image, according to an example embodiment of the present disclosure. At Event A, the image acquirer 408 causes the display interface 414 of the application 108 to display the user interface 502 prompting a user to select an image selection method via the prompt 506. In this example, the user selects the "Take Photo Automatically" option. This selection causes the image acquirer 408 to display the user interface 702.

At Event B, image acquirer 408 causes a photo section 704 to be displayed showing a current image recorded by the camera 106. The photo section 704 includes a prompt for a user to move the user device 102 such that the whole ovulation test device 104 is shown in the photo section 704. The photo section 704 includes alignment brackets 706 that show a user bounds of an image area. The photo section 704 also includes an alignment box 708 that is sized to approximate an ovulation test device 104 as a desired focal distance from the camera 106. The image acquirer 408 determines when the ovulation test device 104 is shown completely within the alignment box 708 using image analysis and/or an image scan. This ensure the handle and test area are adequately captured.

After determining the ovulation test device 104 is within the alignment box 708, the image acquirer 408 causes an image to be recorded by the camera 106. At Event C, the image acquirer 408 provides a confirmation user interface 710, which provides a preview 712 of the recorded image and the image sample 513. The user interface 710 prompts a user to compare the preview 712 to the image sample 513 to ensure the ovulation test device 104 is provided at a cored orientation and the T-line and the C-line are clearly visible and/or in focus. The user interface 710 includes an icon to save the image, which is stored as an image 404 to the memory device 402. Similar to the process flow 500 of FIG. 5, the process flow 700 of FIG. 7 at Event D includes the application 508 and/or the server 112 analyzing the selected image 404 to determine a quantitative T/C ratio (e.g., data point 406). The determined quantitative T/C ratio is displayed adjacent to the image 404 in the results section 504 of the user interface 502.

In some embodiments, the image acquirer 408 of the application 108 and/or the server 112 determines that an analysis cannot be performed on an image to obtain a color intensity ratio and/or a quantitative hormone level. For example, the image acquirer 408 may determine that a C-line and/or T-line are not clearly visible using image analysis. Alternatively, the server 112 may return a value of zero or an error if the color intensity ratio and/or a quantitative hormone level cannot be determined from an image. In these embodiments, the application 108 is configured to display user interface 802 of FIG. 8. The user interface 802 includes a message indicative that the selected image cannot be analyzed. The user interface 802 provides an option for a user to select or re-take another image, as discussed above in connection with FIGS. 5 to 7. The user interface 802 also includes an option for a user to manually enter a color intensity ratio.

Figure 8:
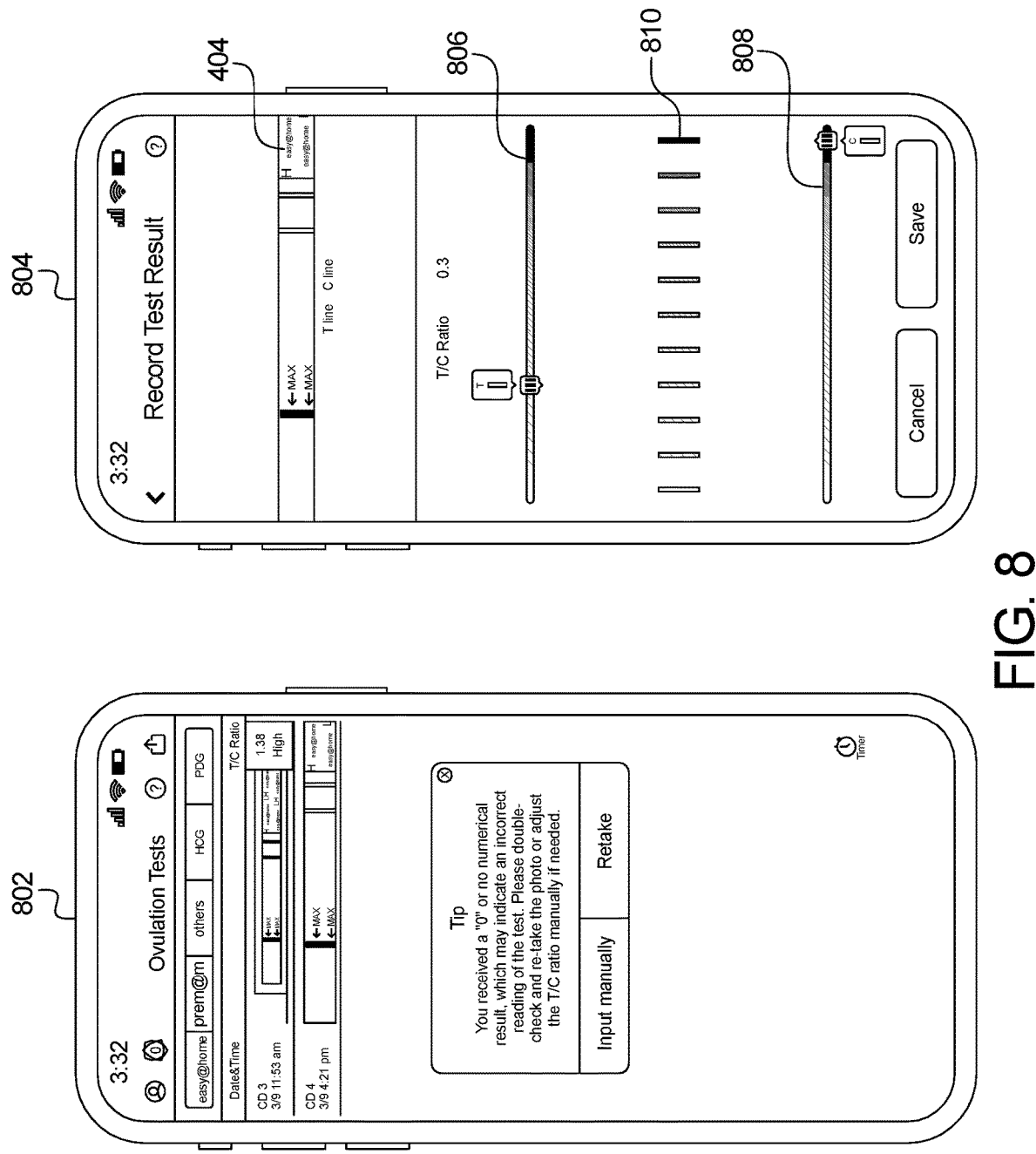
FIG. 8 is a diagram of user interfaces to enable a user to manually enter color intensity ratio information, according to an example embodiment of the present disclosure.

User interface 804 of FIG. 8 is provided by the application 108 to enable a user to manually input a color intensity ratio (i.e., a T/C ratio). The user interface 804 includes the image 404 recorded by the user that generated the error shown in the user interface 802. In this example, light reflection from a portion of the ovulation test device 104 may have affected the image analysis performed by the application 108 and/or the server 112. The user interface 804 also includes a sliding bar 806 for a user to select a T-line value and a sliding bar 808 for a user to select a C-line value. Each of the bars 806 and 808 are colored to approximate possible shading or the T-line and the C-line. The user interface 804 further includes a reference guide 810 showing different shading of the C-line and T-line. In this example, a user is prompted by the user interface 804 to drag an icon along the T-line bar 806 until a color approximates a color of the T-line shown in the image 404. Additionally, a user is prompted by the user interface 804 to drag another icon along the T-line bar 808 until a color approximates a color of the C-line shown in the image 404. The application 108 is configured to determine a color intensity ratio based on positions of the icons along the respective bars 806 and 808. The application 108 stores the determined color intensity ratio as a data point 806 to the memory device 402 for association with the image 404 shown in FIG. 8.

In some embodiments, the application 108 is configured to select a version of the user interface 804 based on which type of ovulation test device 104 was imaged. In some embodiments, the image acquirer 408 determines the test device type, as described above, and accordingly selects a corresponding version of the user interface 804. In another example, the image acquirer 408 displays a user interface prompt for a user to input a type of the ovulation test device 104, which causes the image acquirer 408 to select the corresponding user interface 804.

Figure 9:
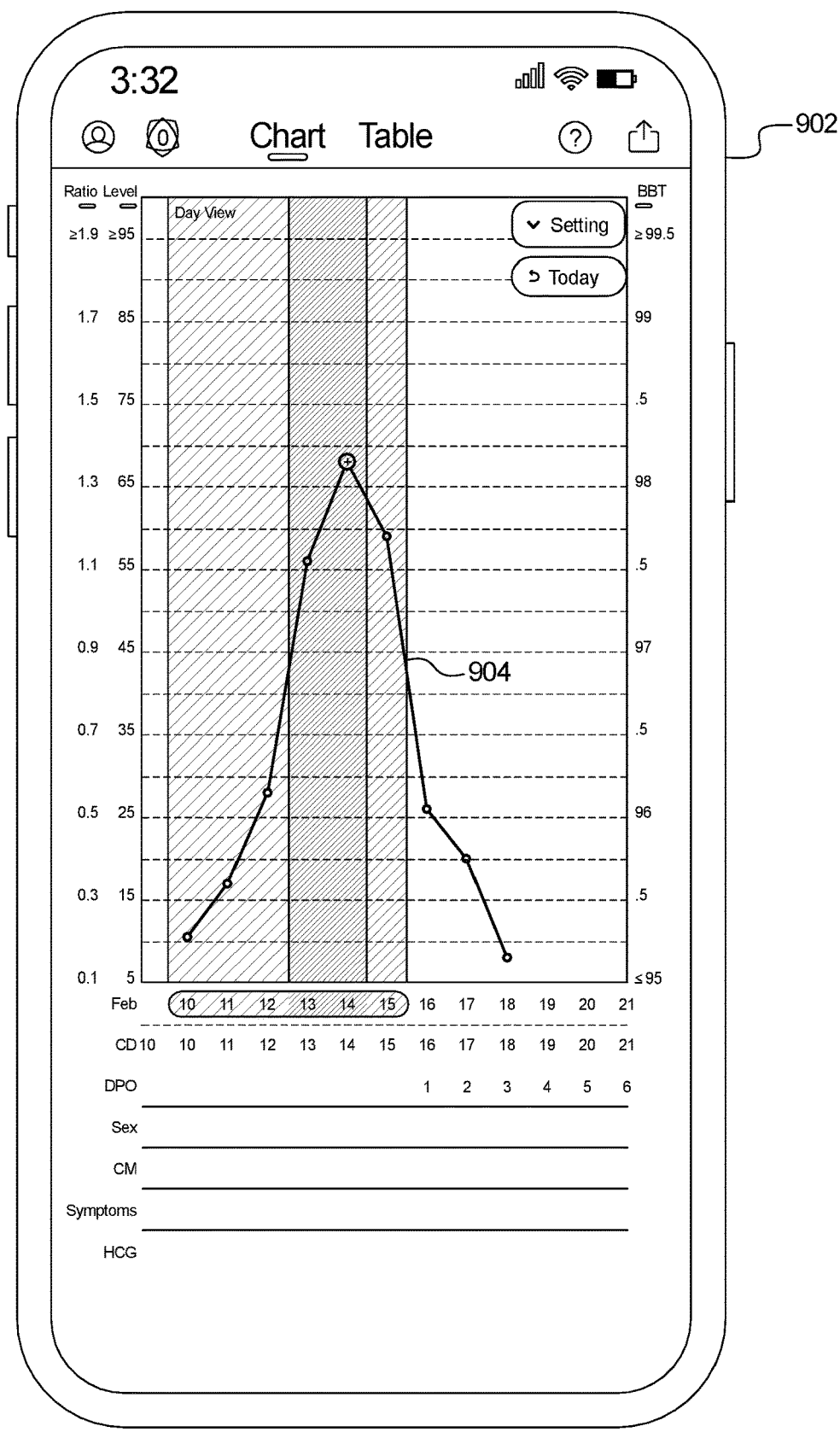
FIG. 9 is a diagram of a user interface created or populated by the application of the user device to show a month of quantitative hormone data points, according to an example embodiment of the present disclosure.

Returning to FIG. 4, the application 108 includes the trend manager 410 to analyze individual data points 406 to determine hormone and/or ovulation patterns of a user. The trend manager 410 may, for example, cause the display interface 414 to display a history of quantitative hormone levels and/or color intensity ratios in a calendar and/or graph. FIG. 9 is a diagram of a user interface 902 created or populated by the trend manager 410 to show a month of quantitative hormone data points 406, according to an example embodiment of the present disclosure. The user interface 902 shows a line graph 904 indicative of quantitative hormone levels and corresponding color intensity ratios for certain days of a month. The user interface 902 also includes shading to indicate high/low values and/or a peak LH level. Such information shows a user how their LH level changes over time and how their LH peaks during their ovulation window.

In some embodiments, the trend manager 410 may analyze quantitative hormone levels and/or color intensity ratios for one or months and/or menstrual cycles. The trend manager 410 may determine which days a user's quantitative hormone levels and/or color intensity ratios are likely to peak and values for that peak. The trend manager 410 may then display a prediction to a user for subsequent months.

Figure 10A:
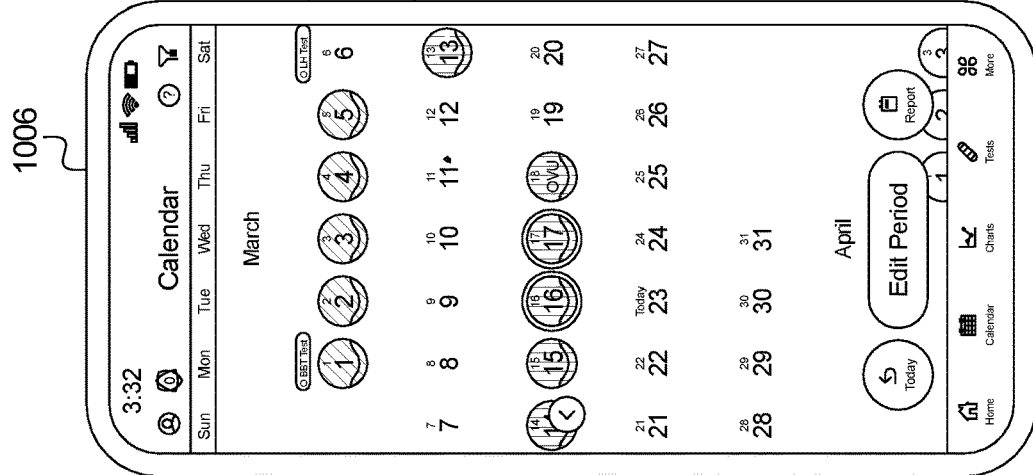
FIGS. 10A-10C are diagrams illustrative of a prediction of a user's high fertility window and possible ovulation date performed by the application of the user device, according to an example embodiment of the present disclosure.
Figure 10B:
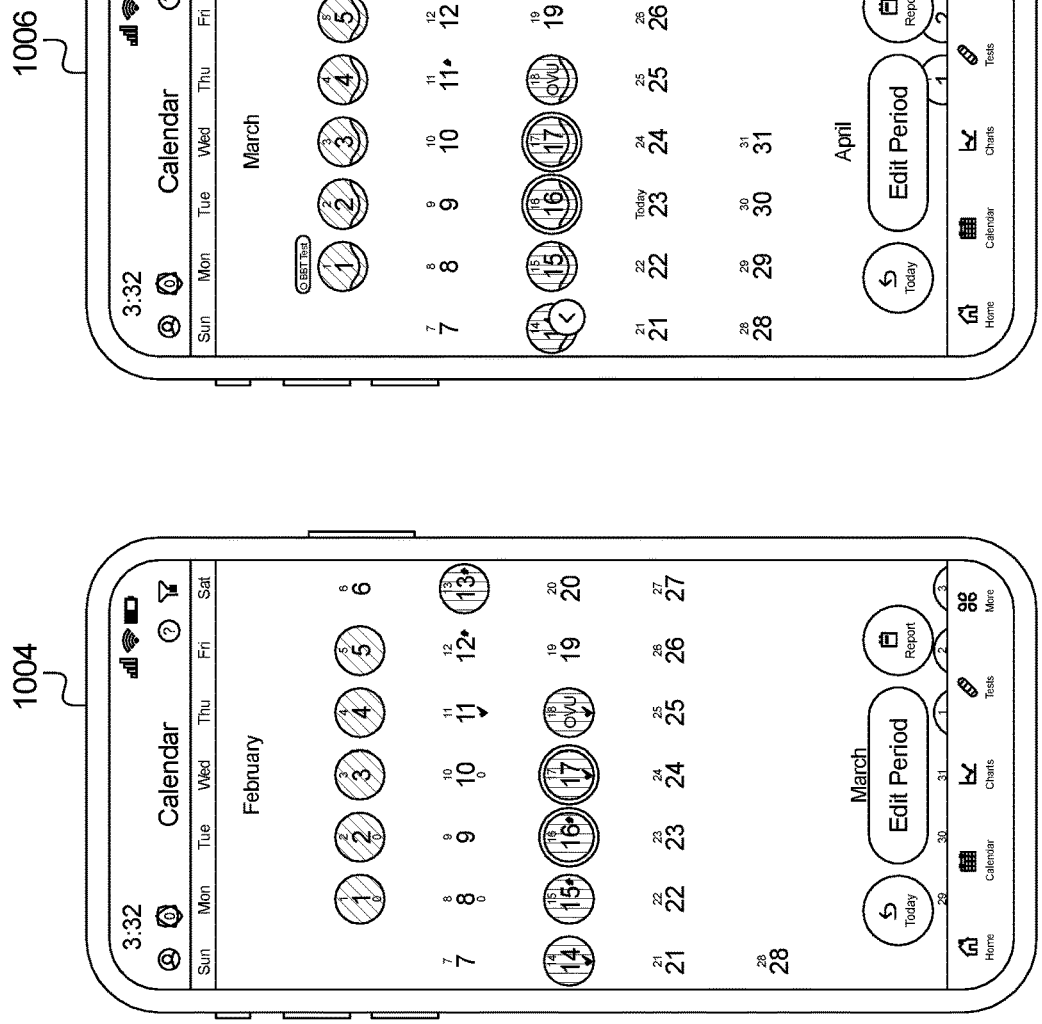
Figure 10C:
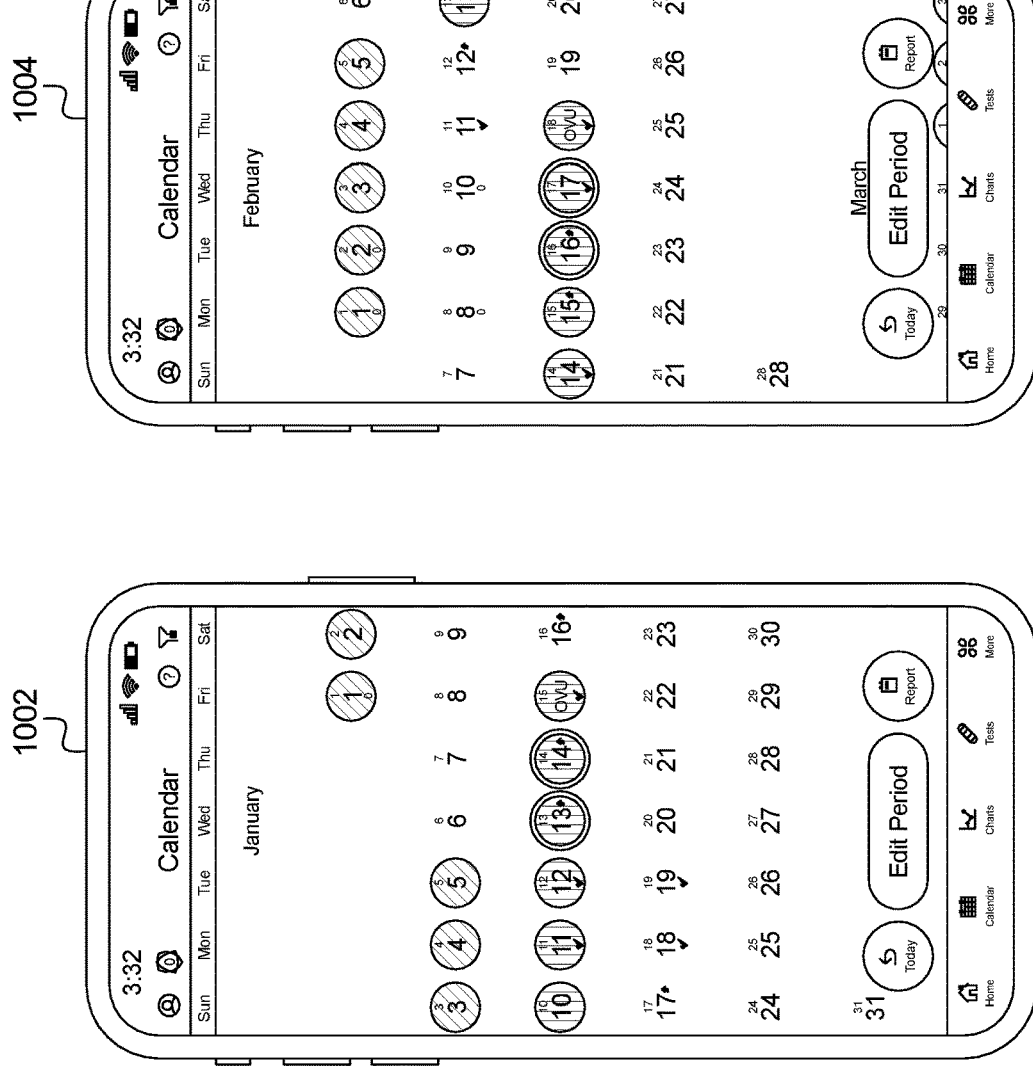

FIGS. 10A-10C are diagrams illustrative of a prediction performed by the trend manager 410 of the application 108 (or the server 112), according to an example embodiment of the present disclosure. In this example, the trend manager 410 determines or receives information indicative that a user experienced a period between January 1 and 5 and another period between February 1 and 5 (indicated by a first shading). Additionally, the trend manager 410 determines from the data points 406 in the memory device 402 that a user had a high fertility window between January 10 and 15 (indicated by a second shading), with peak predicted fertility on January 13 and 14 (indicated by a second shading and a double circle) and a high fertility window between February 13 and 18 (indicated by a second shading), with peak predicted fertility on February 16 and 17 (indicated by a second shading and a double circle). The data points 406 and period indications are shown in user interfaces 1002 and 1004 respectively for January and February. The trend manager 410 averages the starting and ending days from January and February to predict that a user will have a period between March 1 and 5 (indicated by a first shading) and a high fertility window between March 13 and 18 (indicated by a second shading), with peak predicted fertility around March 16 and 17 (indicated by a second shading and a double circle). The predicted high fertility windows, peak predicted fertility, and period days are shown in user interface 1006 for March. In some embodiments, the trend manager 410 predicts fertility windows, peak predicted fertility, and/or period days for a subsequent two, three, or four months.

Returning to FIG. 4, the application 108 of the user device 102 also includes the server interface 412 to enable connectivity with the server 112 of FIG. 1. The server interface 412 is configured to connect to one or more application programming interfaces ("APIs") for transmitting one or more images 404 to the server 112. The server interface 412 is also configured to connect to one or more APIs to receive data points 406 from the server 112. The server interface 412 may also receive updates to one or more thresholds and/or conditions for distinguishing between low/negative, high/positive, and peak fertility windows and dates and/or corresponding color intensity ratios. The server interface 412 may be programmed with an internet address and/or API port identifiers for connecting with the server 112. Further, the server interface 412 may store or manage user credentials for accessing a user account managed by the server 112.

The application 108 of the user device 102 further includes the display interface 414 for displaying the user interfaces 502, 508, 602, 702, 710, 802, 804, 902, 1002, 1004, and/or 1006 of FIGS. 5 to 10. The display interface 414 may manage one or more application templates stored in the memory device 402. The display interface 414 selects a template based on user navigation and accesses the data points 406 and/or images 404 stored in the memory device 402 and/or at the server 112 for populating the selected template with data for producing the above-discussed interfaces. Each template includes fields that define which of the data points 406 and/or images 404 are to be displayed. The display interface 414 is configured to use the fields of the template to populate the specified data for display. The display interface 414 is also configured to receive user inputs for selecting images 404 and/or entering information for operating the application 108.

The example application 108 discussed in connection with FIGS. 4 to 10 accordingly provides an easy to use interface that enables a user to record an image of an ovulation test device 104 and displays corresponding quantitative hormone levels and/or color contrast ratios. The application 108 provides the same interfaces and operability regardless of a type or brand of ovulation test device 104, thereby enabling interoperability with any commercial test strips, mid-stream strips, and/or cassettes. The application 108 also enables a user to track their predicted fertility over the course of multiple months and predict when a user is to be at a peak fertility for a subsequent month.

Management Server Embodiment

Figure 11:
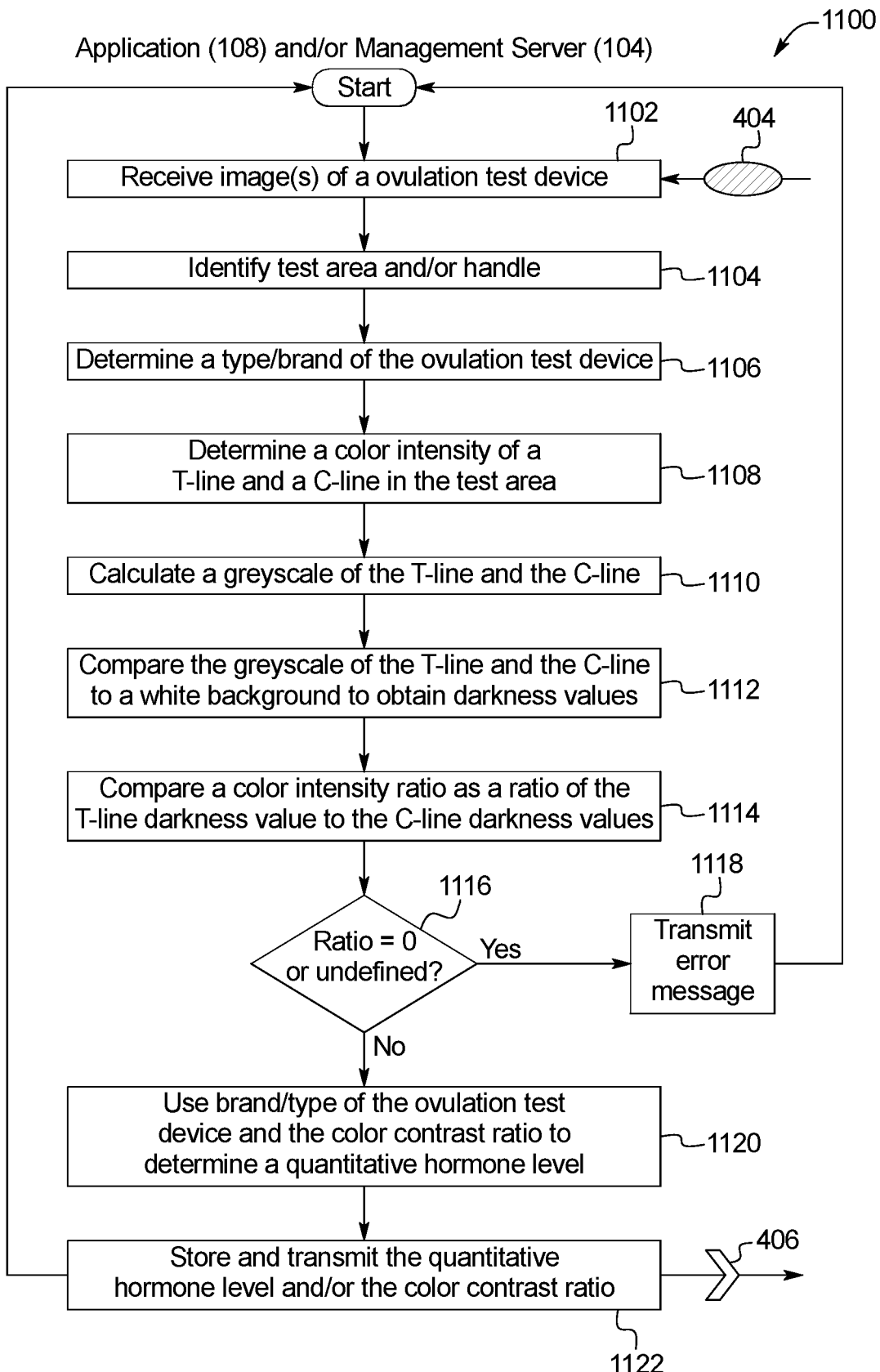
FIG. 11 is a flow diagram of an example procedure for calculating a quantitative hormone level using at least one received image, according to an example embodiment of the present disclosure.

As discussed above, the management server 112 of FIG. 1 is configured to receive one or more selected images 404 from the application 108 on the user device 102, calculate a color intensity ratio, calculate a quantitative hormone level, and transmit the calculated quantitative hormone level and/or the color intensity ratio for display by the application 108. FIG. 11 is a flow diagram of an example procedure 1100 for calculating a quantitative hormone level using at least one received image 404, according to an example embodiment of the present disclosure. Although the procedure 1100 is described with reference to the flow diagram illustrated in FIG. 11, it should be appreciated that many other methods of performing the steps associated with the procedure 1100 may be used. For example, the order of many of the blocks may be changed, certain blocks may be combined with other blocks, and many of the blocks described may be optional. In an embodiment, the number of blocks may be changed. The actions described in the procedure 1100 are specified by one or more instruction and may be performed among multiple devices including, for example, the management server 112, the memory device 116, and/or the application 108 on the user device 102.

The example procedure 1100 begins when the server 112 receives one or more images 404 from the application 108 on the user device 102 (block 1102). In some embodiments, the application 108 is configured to crop the image 404 prior to transmission to the server 112. In other embodiments, the server 112 receives and crops the image 404. The server 112 crops the image by identifying an outline of the ovulation test device 104 (e.g., a rectangular outline). The server 112 then draws a window over at least a portion of the ovulation test device 104 to include the test area 105 and the handle 107. Areas outside the window are removed by the server 112.

The server 112 next analyzes the cropped image to identify the test area 105 and/or the handle 107 (block 1104). The server 112 may use image analysis to search for two parallel lines corresponding to the T-line 109 and the C-line 111 of the test area 105. The server 112 may also identify text and/or graphics to identify the handle 107. The server 112 uses the identified test area 105 and/or the handle 107 to determine a brand and/or type of the ovulation test device 104 shown in the image 404 (block 1106). To determine a brand and/or type, the server 112 may use a BGB color model, a CMYK color model, and/or a CcMmYK color model or other color model to determine a color of the T-line 109 and the C-line 111. The server 112 compares the determined colors to a data structure in the memory device 116 that relates line colors to brand and/or type. Additionally or alternatively, the server 112 matches text and/or graphics shown on the handle 107 to template handles of known brands and/or test device types. The server 112 may, for example, align the handle 107 in the image 404 over templates of known handles and subtract pixel color values between the templates and the handle 107 to determine which template has a lowest value, indicating a match. In other instances, metadata with the image 404 may identify the type and/or brand of the ovulation test device 104.

Figure 12:
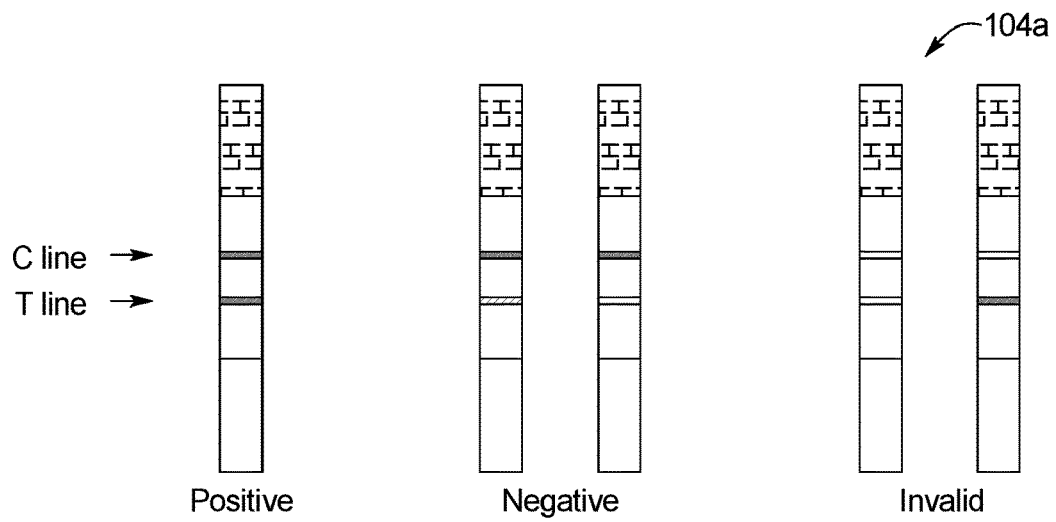
FIGS. 12 to 14 are diagrams of images of different ovulation test devices, according to an example embodiment of the present disclosure.
Figure 13:
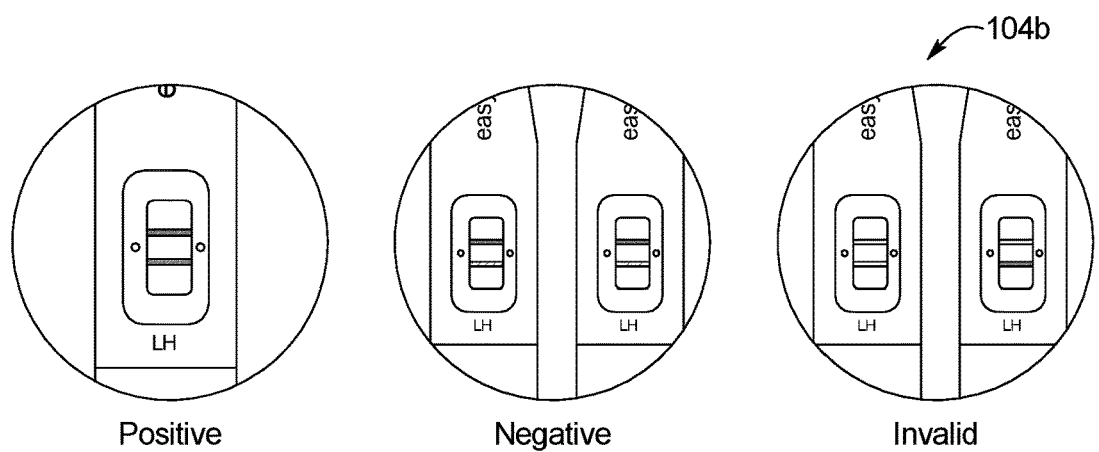
Figure 14:
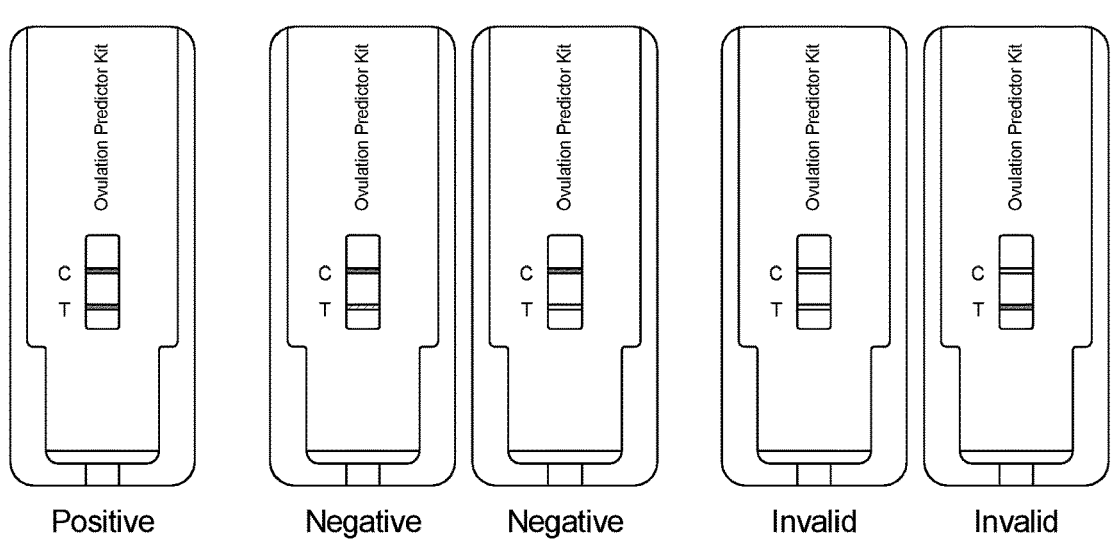

FIGS. 12 to 14 are diagrams of images 404 of different ovulation test devices 104, according to an example embodiment of the present disclosure. The ovulation test devices 104 are configured to receive a urine sample containing LH. The urine sample migrates or flows along a body of the test devices 104 in the test area 105. Depending on the concentration of the analytes in the sample, particles carrying the appropriate binding material become attached to the testing strip in the T-line 109. The degree of binding of the particles can be visually determined by comparing the T-line 109 to the C-line 111.

FIG. 12 shows positive, negative, and invalid results for a test strip ovulation test device 104*a*. FIG. 13 shows positive, negative, and invalid results for a mid-stream strip ovulation test device 104*b*. FIG. 14 shows positive, negative, and invalid results for a test cassette ovulation test device 104*c*. The server 112 is configured to analyze the different images showing T-lines 109 and C-lines 111 in different colors and positions to determine a quantitative hormone value. In other words, the server 112 is compatible with different types and/or brands of ovulation test devices 104, and uses the image analysis described below to determine standardized quantitative hormone values.

In instances where the server 112 has not already calculated color intensities of the T-line 109 and the C-line 111, the procedure 11000 continues by the server 112 identifying the T-line 109 and the C-line 111 using patterning matching and using an RGB color model, a CMYK color model, and/or a CcMmYK color model or other color model to determine a color intensity of the T-line 109 and the C-line 111 (block 1108). The server 112 then calculates or creates a greyscale of at least the T-line 109 and the C-line 111 in the image 404 (block 1110). The server 112 compares the greyscale of the T-line 109 and the C-line 111 to a white background of the image 404 to determine respective darkness values (block 1112). The server 112 then calculates a color intensity ratio as a ratio of the darkness value of the T-line 109 to the darkness value of the C-line 111 (block 1114).

The server 112 determines if the color intensity ratio has an undefined value or a value of zero (block 1116). This check determines if there was an issue analyzing the received image 404. If the ratio has a value of zero or is undefined, the server 112 transmits an error message to the application 108 on the user device 102 (block 1118). The error message may cause the application 108 to display the user interface 802 of FIG. 8 to indicate that a new image should be selected/acquired and/or that a quantitative T/C ratio should be manually entered. The procedure 1100 continues by the server 112 receiving another image 404 of an ovulation test device 104.

If the color intensity value is greater than zero, the server 112 is configured to access the data structure 118 in the memory device 114 (block 1120). The server 112 uses the identified brand/or type of the test device 104 to select a table or file of the corresponding type or brand. The server 112 than matches the color intensity ratio to a same or similar color intensity ratio in the selected table or file. The server 112 determines the quantitative hormone level that corresponds to the matched color intensity ratio. The server 112 next stores the quantitative hormone level and/or the color intensity ratio as a data point 406 to the memory device 116 (block 1122). The server 112 also transmits a message to the application 108 that is indicative of the quantitative hormone level and/or the color intensity ratio, which is stored by the application 108 as the data point 406 in the memory device 402. The server 112 then restarts the example procedure 1100 when another image 404 is received of an ovulation test device 104.

Figure 17:
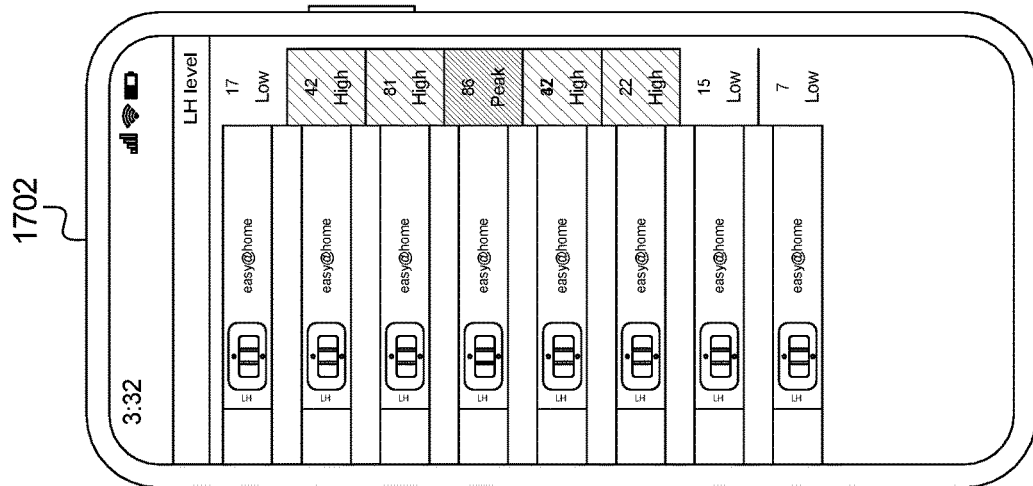
FIGS. 15 to 17 are diagrams of user interfaces showing quantitative hormone level obtained by a user over a month or menstrual cycle, according to an example embodiment of the present disclosure.
Figure 16:
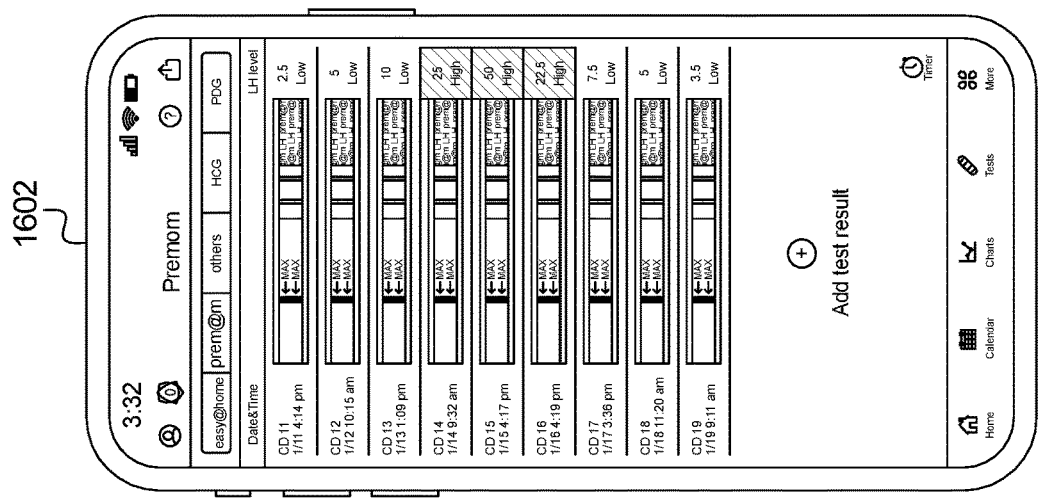
Figure 15:
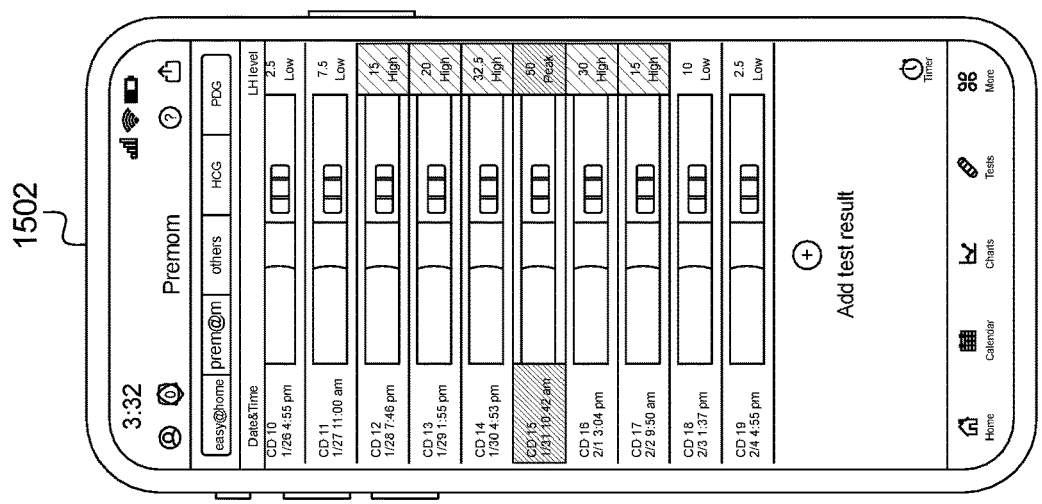
Figure 19:
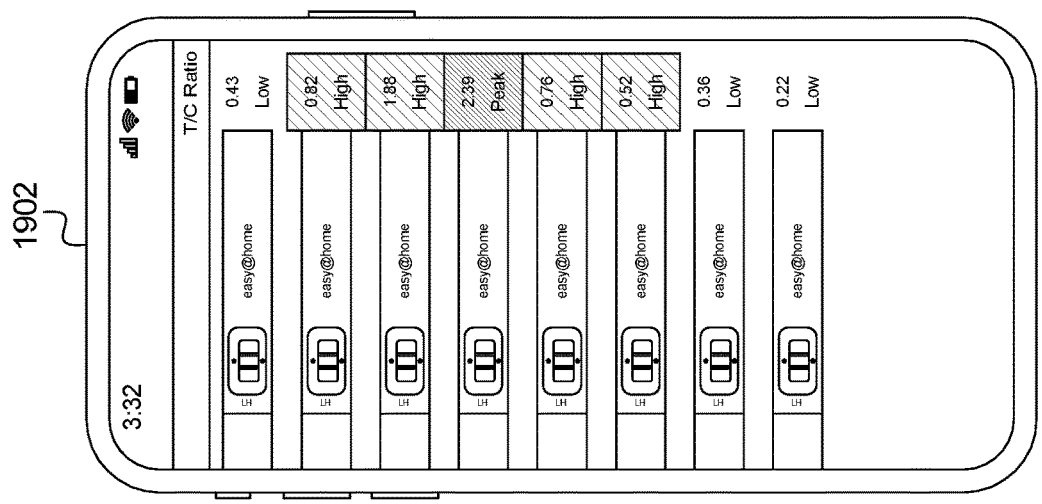
FIGS. 18 to 19 are diagrams of user interfaces showing the quantitative color intensity ratio obtained by a user over a month or menstrual cycle, according to an example embodiment of the present disclosure.
Figure 18:
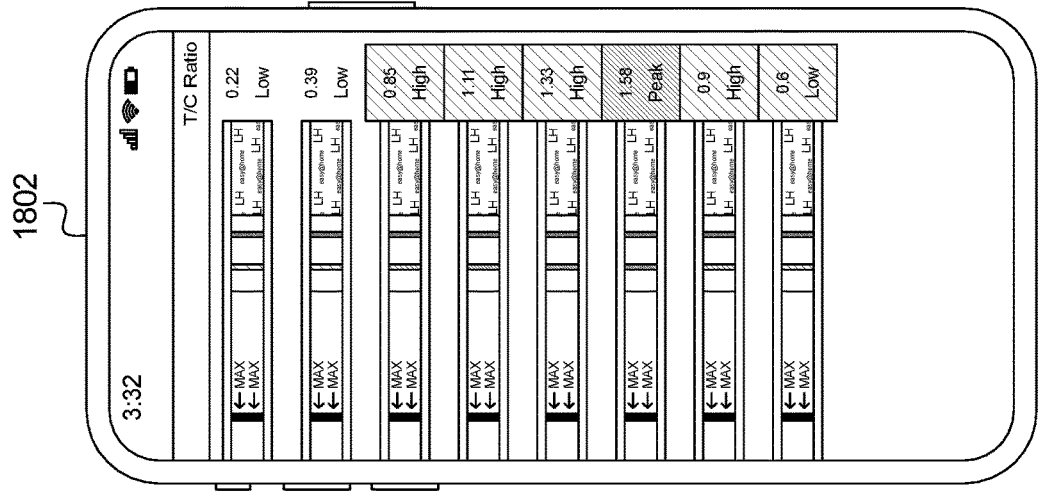

FIGS. 15 to 17 are diagrams of user interfaces showing quantitative hormone level obtained by a user over a month or menstrual cycle, according to an example embodiment of the present disclosure. FIGS. 18 to 19 are diagrams of user interfaces showing the quantitative color intensity ratio obtained by a user over a month or menstrual cycle, according to an example embodiment of the present disclosure. Each of the user interfaces are displayed by the application 108 using data points 406 provided by the server 112. Each of the user interfaces include a value of the quantitative hormone level and/or the color intensity ratio, a color coding (shown as shading in the FIGS.) for the quantitative hormone level and/or the color intensity ratio, and a cropped image 404 that produced the quantitative hormone level and/or the color intensity ratio.

FIG. 15 is a diagram of a user interface 1502 that shows quantitative hormone level in association with an image 404. Each row in the user interface 1502 corresponds to a separate ovulation test and includes a date/time an image was recorded, a cropped version of the recorded image 404, and the quantitative hormone level showing a numerical value and a background color of white, pink (represented by shading in the FIGS.), or purpose based on the test result. In FIG. 15, the ovulation test device 104 is a cassette. By contrast, FIG. 16 shows a user interface 1602 for a test strip ovulation test device 104. Similar to FIG. 15, the user interface 1602 of FIG. 16 shows quantitative hormone levels for different test days and corresponding recorded images 404. FIG. 17 is a diagram of another user interface 1702 for a mid-stream ovulation test device 104.

FIGS. 18 and 19 show user interfaces 1802 and 1902 where color intensity ratios are displayed instead of quantitative hormone levels. Similar to the user interfaces 1502 to 1702, the color intensity ratios are shown with a background color of white, pink (represented by a first shading in the FIGS.), or purple (represented by a second shading in the FIGS.) corresponding to a high, low, or peak LH level. The user interface 1802 shows a test strip ovulation test device 104 and the user interface 1902 shows a mid-stream ovulation test device 104.

In some embodiments, the server 112 is configured to determine a peak LH level. The server 112 may analyze LH levels of the same month to determine a local maximum quantitative hormone level and/or color intensity value. The server 112 labels the test result corresponding to the peak as a peak value. The server 112 may store the indication of the peak value to the data point 406 when transmitted to the application 108. Alternatively, the application 108 may determine the peak LH value. As shown in FIGS. 15 and 17, the peak designation causes the user interface 1502 and 1702 to provide a purple background (represented by shading in the FIGS.) and provide a peak identification for the corresponding test row.

Figure 20:
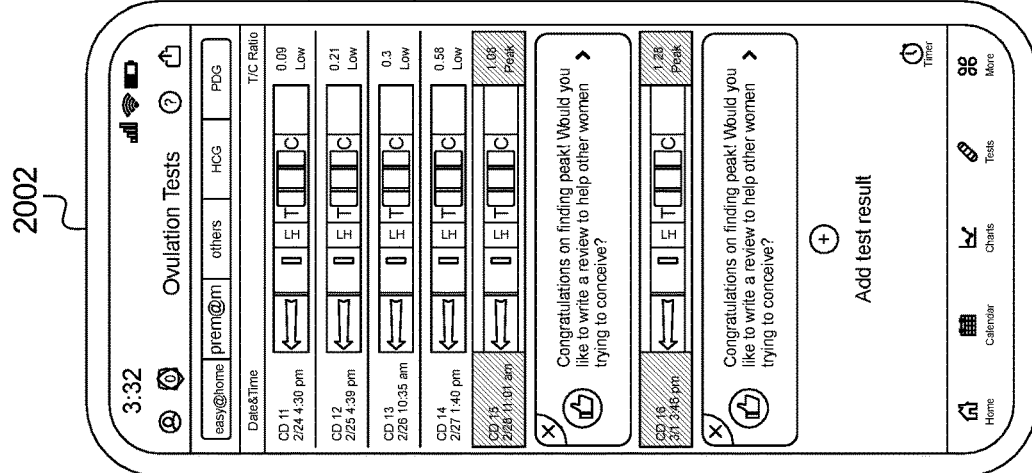
FIG. 20 is a diagram of a user interface providing a highlight of LH peak identification based on the T/C ratio trend, according to an example embodiment of the present disclosure.

FIG. 20 is a diagram of a user interface 2002 providing a highlight of LH peak identification, according to an example embodiment of the present disclosure. The user interface 2002 provides a congratulations message in addition to identifying a peak test result row. The message includes a link to enable a user to provide a review and/or recommendation. In some instances, a user may provide feedback as to whether identification of the peak LH level helped cause conception.

In additional embodiments, the server 112 is configured to predict a user's high fertility dates and/or peak fertility dates using data points 406 from one or more previous or current months. In these examples, the server 112 determines a predicted high fertility window and possible ovulation date for a next month based on the measured cycle length, high fertility window, and predicted ovulation date in prior months. The server 112 transmits a message to the application 108 with the predicted high fertility window, including identification of days with high and/or peak LH levels, as shown in the user interface 1006 of FIG. 10.

The example server 112 may also personalize a threshold between low/high LH levels for a user. For example, the default or normal threshold may correspond to a color intensity ratio of 0.8. However, the server 112 detects for one or more months that a T/C ratio for a user's peak or high fertility level is less than 0.8. The server 112 accordingly reduces the threshold to 0.5 or 0.6 to account for a user's relatively low LH levels, even during times of peak ovulation. The server 112 may repeat the process if it is detected that the T/C ratio at subsequent peak LH levels fail to exceed a ratio of 0.5. The server 112 may transmit an indication of the threshold to the application 108 for color coding the test results. In this manner, the server 112 accordingly adapts the high/low threshold to a user's own hormone trends.

Conclusion

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A testing system comprising:
    a test device including a test area including a visually identifiable test-line and a visually identifiable control-line formed in response to exposure to a tested substance, the test area further includes a background; and
    a user device including a camera, a processor, a display, and memory storing program instructions, wherein, in response to executing the program instructions, the processor:
        receives an image of the test device from the camera, the image including the test area, the visually identifiable test-line, and the visually identifiable control-line;
        creates a test-line greyscale representation of the visually identifiable test-line and a control-line greyscale representation of the visually identifiable control-line;
        determines a numerical test-line value by comparing a test-line darkness value of the test-line greyscale representation of the visually identifiable test-line to the background of the test area to control for ambient interference and lighting conditions;
        determines a numerical control-line value by comparing a control-line darkness value of the control-line greyscale representation of the visually identifiable control-line to the background of the test area to control for the ambient interference and lighting conditions; and
        calculates a T/C ratio defined as a relative value of the numerical test-line value to the numerical control-line value.

2. The system of claim 1, wherein, in response to executing the program instructions, the processor further:
    creates a second test-line greyscale representation of a second visually identifiable test-line;
    determines a second numerical test-line value by comparing a second test-line darkness value of the second test-line greyscale gray scale representation of the second visually identifiable test-line to the background of the test area to control for the ambient interference and lighting conditions; and
    calculates a second T/C ratio defined as a second relative value of the second numerical test-line value to the numerical control-line value.

3. The system of claim 1, wherein the test device is a rapid lateral flow immunoassay test device that is one of an ovulation, pregnancy, progesterone, estrogen, estriol, and follicle-stimulating hormone test device.

4. The system of claim 1, wherein the tested substance is one of urine, blood, and saliva.

5. The system of claim 1, wherein, in response to executing the program instructions, the processor selects the image from a stream of images received from the camera.

6. The system of claim 1, wherein the image includes a visually identifiable portion of the test device, further wherein, in response to executing the program instructions, the processor identifies a model of the test device based on the visually identifiable portion of the test device.

7. The system of claim 6, wherein the processor identifies the visually identifiable test-line and the visually identifiable control-line by identifying a location, edges, and a line width within the test area that correspond to a defined test-line and a defined control-line for the identified model of the test device.

8. The system of claim 1, wherein the processor is configured to present information indicative of the T/C ratio, wherein the information indicative of the T/C ratio includes a calendar and/or a graph including information indicative of an ovulation cycle and/or hormone changes over time of a user.

9. The system of claim 1, wherein the memory stores a data structure that relates the T/C ratio to quantitative levels of tested substance.

10. The system of claim 9, wherein a characteristic being tested is the presence of one or more of a luteinizing hormone, a human chorionic gonadotropin, progesterone, estrogen, estriol, and a follicle-stimulating hormone in the tested substance.

11. The system of claim 10, wherein the T/C ratio is translated into a quantitative level of tested substance.

12. The system of claim 11, wherein the processor is configured to present information indicative of the quantitative level of the tested substance, wherein the information includes a calendar and/or a graph including information indicative of an ovulation cycle and/or hormone changes over time of a user.

13. A testing system comprising:
a test device including a test area including a visually identifiable test line and a visually identifiable control line formed in response to exposure to a tested substance, the test area further includes a background; and
a camera, including an image capture mechanism and a camera communication interface;
a processor, including an image processing mechanism and a processor communication interface in communication with the camera communication interface; and
a display controlled by the processor:
wherein, in response to executing the program instructions, the processor:
receives an image of the test device from the camera, the image including the test area, the visually identifiable test-line, and the visually identifiable control-line;
creates a test-line greyscale representation of the visually identifiable test-line and a control-line greyscale representation of the visually identifiable control-line;
determines a numerical test-line value by comparing a test-line darkness value of the test-line greyscale representation of the visually identifiable test-line to the background of the test area to control for ambient interference and lighting conditions;
determines a numerical control-line value by comparing a control-line darkness value of the control-line greyscale representation of the visually identifiable control-line to the background of the test area to control for ambient interference and lighting conditions; and
calculates a T/C ratio defined as a relative value of the numerical test-line value to the numerical control-line value.

14. The system of claim 13, wherein, in response to executing the program instructions, the processor further:
creates a second test-line greyscale representation of a second visually identifiable test-line;
determines a second numerical test-line value by comparing a second test-line darkness value of the second test-line greyscale representation of the second visually identifiable test-line to the background of the test area to control for ambient interference and lighting conditions; and
calculates a T/C ratio defined as a second relative value of the second numerical test-line value to the numerical control-line value.

15. The system of claim 13, wherein the test device is a rapid lateral flow immunoassay test device that is one of an ovulation, pregnancy, progesterone, estrogen, estriol, and follicle-stimulating hormone test device.

16. The system of claim 13, wherein the tested substance is one of urine, blood, and saliva.

17. The system of claim 13, wherein, in response to executing the program instructions, the processor selects the image from a stream of images received from the camera.

18. The system of claim 13, wherein the image includes a visually identifiable portion of the test device, further wherein, in response to executing the program instructions, the processor identifies a model of the test device based on the visually identifiable portion of the test device.

19. The system of claim 18, wherein the processor identifies the visually identifiable test-line and the visually identifiable control-line by identifying a location, edges, and a line width within the test area that correspond to a defined test-line and a defined control-line for the identified model of the test device.

20. The system of claim 13, wherein the processor is configured to present information indicative of the T/C ratio, wherein the information includes a calendar and/or a graph including information indicative of an ovulation cycle and/or hormone changes over time of a user.

21. The system of claim 13, wherein the memory stores a data structure that relates T/C ratio to quantitative levels of tested substance.

22. The system of claim 21, wherein a characteristic being tested is the presence of one or more of a luteinizing hormone, a human chorionic gonadotropin, progesterone, estrogen, estriol, and a follicle-stimulating hormone in the tested substance.

23. The system of claim 13, wherein the T/C ratio is translated into a quantitative level of the tested substance.

24. The system of claim 23, wherein the processor is configured to present information indicative of the quantitative level of the tested substance, wherein the information includes a calendar and/or a graph including information indicative of an ovulation cycle and/or hormone changes over time of a user.

* * * * *